United States Patent
Claremon et al.

(10) Patent No.: US 6,870,055 B2
(45) Date of Patent: Mar. 22, 2005

(54) ISOQUINOLINONE POTASSIUM CHANNELS INHIBITORS

(75) Inventors: David A. Claremon, Maple Glen, PA (US); Charles J. McIntyre, Lansdale, PA (US); Nigel J. Liverton, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 6 days.

(21) Appl. No.: 10/362,484

(22) PCT Filed: Sep. 17, 2001

(86) PCT No.: PCT/US01/29013

§ 371 (c)(1),
(2), (4) Date: Feb. 25, 2003

(87) PCT Pub. No.: WO02/24655

PCT Pub. Date: Mar. 28, 2002

(65) Prior Publication Data

US 2004/0044030 A1 Mar. 4, 2004

Related U.S. Application Data

(60) Provisional application No. 60/234,389, filed on Sep. 20, 2000.

(51) Int. Cl.[7] .................... C07D 217/22; C07D 217/02; A61K 31/47
(52) U.S. Cl. ........................ 546/141; 546/142; 514/309; 514/307
(58) Field of Search ................................ 514/309, 307; 546/141, 142

(56) References Cited

U.S. PATENT DOCUMENTS 5,482,967 A * 1/1996 Natsugari et al. ........... 514/457

FOREIGN PATENT DOCUMENTS

| EP | 0 481 383 A1 | | 4/1992 |
|---|---|---|---|
| EP | 0 585 913 A2 | | 3/1994 |
| EP | 0 634 402 A1 | | 1/1995 |
| EP | 0 634 402 | * | 1/1995 |
| EP | 0 634 602 A1 | | 1/1995 |
| WO | WO 98/38168 | * | 9/1998 |
| WO | WO00/25774 | | 5/2000 |

OTHER PUBLICATIONS

Ashton, CA 112:158072, abstract of EP 326386, 1989.*

Natsukari, CA 115:158988, abstract of JP 03112967, 1991.*

* cited by examiner

*Primary Examiner*—D. Margaret Seaman
(74) *Attorney, Agent, or Firm*—Richard S. Parr; Valerie J. Camara

(57) ABSTRACT

The present invention concerns certain isoquinolinone compounds and their utility as inhibitors of voltage-dependent potassium channels or currents, such as $K_v1.5$ and $I_{Kur}$, that could serve as targets for the treatment of cardiac arrhythmias especially atrial arrhythmias. The present invention also provide a method for treating or preventing conditions which respond to the inhibition of potassium channels or currents, such as cardiac arrhythmias and more especially atrial arrhythmias. The present invention further includes pharmaceutical formulations and a process of making a pharmaceutical composition comprising a compound of certain isoquinolinone or its pharmaceutically acceptable salts, hydrates, solvates, crystal forms, and stereoisomers thereof, and a pharmaceutically acceptable carrier.

10 Claims, No Drawings

ISOQUINOLINONE POTASSIUM CHANNELS INHIBITORS

The application claims the benefit of Provisional application Ser. No. 60/234,389, filed Sep. 20, 2000.

FIELD OF THE INVENTION

The present invention is directed to class of isoquinolinone compounds that are useful as potassium channel inhibitors, which show antiarrhythmic properties.

BACKGROUND OF THE INVENTION

Mammalian cell membranes perform very important functions relating to the structural integrity and activity of various cells and tissues. Of particular interest in membrane physiology is the study of trans-membrane ion channels which act to directly control a variety of physiological, pharmacological and cellular processes. Numerous ion channels have been identified including calcium (Ca), sodium (Na) and potassium (K) channels, each of which have been analyzed in detail to determine their roles in physiological processes in vertebrate and insect cells.

A great deal of attention has been focused on potassium channels because of their involvement in maintaining normal cellular homeostasis. A number of these potassium channels open in response to changes in the cell membrane potential. Many voltage-gated potassium channels have been identified and are distinguishable based on their electrophysiological and pharmacological properties. Potassium currents have been shown to be more diverse than sodium or calcium currents and also play a role in determining the way a cell responds to an external stimulus. The diversity of potassium channels and their important physiological role highlights their potential as targets for developing therapeutic agents for various diseases.

Inhibitors of potassium channels lead to a decrease in potassium ion movement across cell membranes. Consequently, such inhibitors induce prolongation of the electrical action potential or membrane potential depolarization in cells containing the inhibited or blocked potassium channels. Prolonging of the electrical action potential is a preferred mechanism for treating certain diseases, e.g., cardiac arrhythmias (Colatsky et al., Circulation 82:223 5, 1990). Membrane potential depolarization is a preferred mechanism for the treating of certain other diseases, such as those involving the immune system (Kaczorowski and Koo, Perspectives in Drug Discovery and Design, 2:233, 1994). In particular, blocking potassium channels has been shown to regulate a variety of biological processes including cardiac electrical activity (Lynch et al., FASEB J 6:2952, 1992; Sanguinetti, Hypertension 19:228, 1992; Deal et al., *Physiol. Rev.* 76:49, 1996), neurotransmission (Halliwell, "K⁺ Channels in the Central Nervous System" in Potassium Channels, Ed. N. S. Cook, pp348, 1990), and T cell activation (Chandy et al., *J. Exp. Med.* 160:369, 1984; Lin et al., *J. Exp. Med.* 177:637, 1993). These effects are mediated by specific subclasses or subtypes of potassium channels.

Potassium channels have been classified according to their biophysical and pharmacological characteristics. Salient among these are the voltage dependent potassium channels, such as $K_v1$. The $K_v1$ class of potassium channels is further subdivided depending on the molecular sequence of the channel, for example $K_v1.1$, $K_v1.3$, and $K_v1.5$. Functional voltage-gated K⁺ channels can exist as multimeric structures formed by the association of either identical or dissimilar subunits. This phenomena is thought to account for the wide diversity of K⁺ channels. However, subunit compositions of native K⁺ channels and the physiologic role that particular channels play are, in most cases, still unclear.

Atrial fibrillation (AF) is the most common sustained cardiac arrhythmia in clinical practice and is likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches.

Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class Of Anti-Arrhythmic Action: Effects On Atrial And Ventricular Intracellular Potentials And Other Pharmacological Actions On Cardiac Muscle, of MJ 1999 and AH 3747" *Br. J. Pharmacol* 1970; 39:675–689 and Singh, B. N., Vaughan Williams E. M., "The Effect Of Amiodarone, A New Anti-Anginal Drug, On Cardiac Muscle", *Br J. Pharmacol* 1970; 39:657–667.), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited-by side effects (Nademanee, K. "The Amiodarone Odyssey". *J. Am. Coll. Cardiol.* 1992; 20:1063–1065.) Drugs of this class are expected to be effective in preventing ventricular fibrillation. Selective Class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. Na⁺ or Ca²⁺ currents; hereinafter $I_{Na}$ and $I_{Ca}$, respectively) or by reducing outward repolarizing potassium (K⁺) currents. The delayed rectifier ($I_K$) K⁺ current is the main outward current involved in the overall repolarization process during the action potential plateau, whereas the transient outward ($I_{to}$) and inward rectifier ($I_{K1}$) K⁺ currents are responsible for the rapid initial and terminal phases of repolarization, respectively. Cellular electrophysiologic studies have demonstrated that $I_K$ consists of two pharmacologically and kinetically distinct K⁺ current subtypes, $I_{Kr}$ (rapidly activating and deactivating) and $I_{Ks}$ (slowly activating and deactivating) (Sanguinetti and Jurkiewicz, "Two Components Of Cardiac Delayed Rectifier K⁺ Current: Differential Sensitivity To Block By Class III Antiarrhythmic Agents," *J. Gen. Physiol.* 1990, 96:195–215). Class III antiarrhythmic agents, including d-sotalol and dofetilide predominantly, if not exclusively, block $I_{Kr}$. Although, amiodarone is a blocker of $I_{Ks}$ (Balser, J. R. Bennett, P. B., Hondeghem, L. M. and Roden, D. M. "Suppression Of Time-Dependent Outward Current In Guinea Pig Ventricular Myocytes: Actions Of Quinidine And Amiodarone." *Circ. Res.* 1991, 69:519–529), it also blocks $I_{Na}$ and $I_{Ca}$, affects thyroid function, is a nonspecific adrenergic blocker, and acts as an inhibitor of the enzyme phospholipase (Nademanee, K. "The Amiodarone Odyssey". *J. Am. Coll. Cardiol.* 1992; 20:1063–1065). Therefore, its method of treating arrhythmia is uncertain.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents, such as d-sotalol and dofetilide predominantly, if not exclusively, block $I_{Kr}$, the rapidly activating component of $I_K$ found both in atria and ventricles in man.

Since these $I_{Kr}$ blockers increase APD and refractoriness both in atria and ventricles without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy," *Am. J. Cardiol.* 1993; 72:44B–49B).

The ultra-rapidly activating delayed rectifier K+ current ($I_{Kur}$) is believed to represent the native counterpart to a cloned potassium channel designated $K_v1.5$ and, while present in human atria, it appears to be absent in human ventricles. Furthermore, because of its rapidity of activation and limited slow inactivation, $I_{Kur}$ is believed to contribute significantly to repolarization in human atria and thus is a candidate potassium channel target for the treatment of cardiac arrhythmias especially those occurring in the atria. (Wang et al., *Circ. Res.* 73:1061, 1993; Fedida et al., *Circ. Res.* 73:210, 1993; Wang et al., *J. Phartnacol. Exp. Aer.* 272:184, 1995; Amos et al., *J. Physiol.,* 491:31, 1996). Consequently, a specific blocker of $I_{kur}$ that is a compound which blocks $K_v1.5$, would overcome the shortcoming of other compounds by prolonging refractoriness in human atria without prolonging ventricular refractoriness that underlie arrhythmogenic after depolarizations and acquired long QT syndrome observed during treatment with current Class III drugs.

Natsugari et al. (EP 0481383) discloses the heterocyclic amine derivatives having an activity of inhibiting acyl-CoA: cholesterol acyltranferase, controlling in mammals, absorption of cholesterol from the intestinal tract and suppressing accumulation of cholesterol ester at the arterial wall thus being useful for prophylaxis and therapy of hypercholesterolemia, atherosclerosis and various diseases caused by them (e.g. ischemic heart diseases such as cardiac infarction and cerebral blood vessel disorders such as cerebral infarction, apoplexy, etc.).

Natsugari, et al. (EP 0585913) is directed to phenyl substituted heterocyclic compounds which are inhibitors of acylCoA: cholesterol transferase (ACAT) and antagonists of tachykinin receptors, and pharmaceutical compositions containing these compounds, process for preparing these compounds, and the use of these compounds for preparing medicaments for treating hypercholesterolemia and artherosclerosis, and for treating pain, disturbance of micturition and inflammation. Natsugari et al. (*J. Med. Chem.* 38:16; 1995; 3106–3120, "Novel Potent, and Orally Active Substance P Antagonists: Synthesis and Antagonist Activity of N-Benzylcarboxamide Derivatives of Pyrido[3,4-b] pyridine") relates to a synthesis of 4-phenylisoquinolone derivatives and $NK_1$ (substance P) antagonist activity of the compounds.

Castle et al. (WO 99/62891) discloses certain thiazolidinone and methathiazanone compounds that are useful as potassium channel inhibitors and for the treatment of cardiac arrhythmias and other diseases, conditions and disorders.

An object of the present invention is directed to the compounds that are useful as inhibitors of potassium channel function and are selective for atrial tissue avoiding side effects of affecting ventricular repolarization. The potassium channel inhibitors of the present invention may therefore be utilized for the treatment of diseases in which prolongation of cellular action potentials would be beneficial, such as cardiac arrhythmia, and particularly atrial arrhythmia.

SUMMARY OF THE INVENTION

This invention relates to compounds of general structural Formula I:

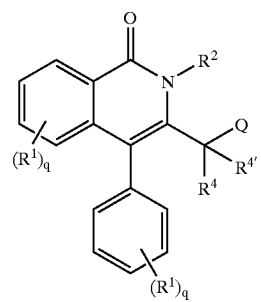

I or a pharmaceutically acceptable salts, hydrates, solvates, crystal forms, or stereoisomers thereof, for use as a $K_v1.5$ potassium channel inhibitor or a $I_{Kur}$ potassium current inhibitor.

The compounds of this invention are useful in the treatment of cardiac arrhythmia and more specifically atrial arrhythmia in a mammal, which comprises administering a therapeutically effective amount of a compound of Formula I. Also within the scope of this invention is pharmaceutical formulations comprising a compound of Formula I and a pharmaceutical carrier. The present invention further includes a process of making a pharmaceutical composition comprising a compound of Formula I or its pharmaceutically acceptable salts, hydrates, solvates, crystal forms, and stereoisomers thereof and a pharmaceutically acceptable carrier.

DETAILED DESCRIPTION OF THE INVENTION

The present invention concerns certain isoquinolinone compounds and their utility as inhibitors of voltage-dependent potassium channels or currents, such as $K_v1.5$ and $I_{Kur}$, that could serve as targets for the treatment of cardiac arrhythmias especially those occurring in the atria (e.g., atrial flutter and atrial fibrillation). Additionally, the present invention also provide a method for treating conditions which respond to the inhibition of potassium channels or currents, such as cardiac arrhythmias and more especially atrial arrhythmias.

An embodiment of the present invention is a compound of structural Formula I:

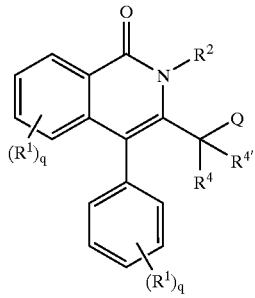

I or a pharmaceutically acceptable salts, hydrates, solvates, crystal forms, or stereoisomers thereof, wherein:

$R^1$ is:
(1) hydrogen,
(2) $(C_1–C_6)$-alkoxy,
(3) $(C_1–C_4)$-perfluoroalkyl,
(4) $(C_1–C_4)$-perfluoroalkoxy, or
(5) halo, wherein halo is fluoro, chloro, bromo, or iodo;

$R^2$ is:
(1) $(C_1–C_6)$-alkyl,
(2) $(CH_2)_n—(T)[S(O)_m]_pR^3$, or
(3) $(CH_2)_n—(T)COR^3$;

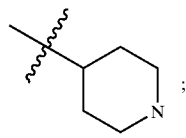

wherein T is —NH or;
n is: 1, 2, or 3;
m is: 0, 1, or 2;
p is: 0 or 1;
q is: 1, 2, 3, or 4;

$R^3$ is:
(1) aryl, wherein aryl is defined as phenyl or naphthyl which is optionally substituted with one, two or three of the substituents selected from the group consisting of:
  (a) halo, wherein halo is fluoro, chloro, bromo, or iodo,
  (b) $(C_1–C_6)$-alkyl,
  (c) $(C_1–C_6)$-alkoxy,
  (d) $(C_1–C_4)$-perfluoroalkyl,
  (e) $(C_1–C_4)$-perfluoroalkoxy,
  (f) phenyl, and
  (g) benzyl;
(2) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of:
  (a) halo, as defined above,
  (b) $(C_1–C_6)$-alkyl,
  (c) $(C_1–C_4)$-perfluoroalkyl, and
  (d) $(C_1–C_6)$-alkoxy;
(3) $(C_1–C_6)$-alkyl optionally substituted with phenyl; or
(4) $(C_1–C_6)$-alkoxy;

$R^4$ and $R^{4'}$ are independently:
(1) H,
(2) $(C_1–C_4)$-alkyl,
(3) $(C_3–C_7)$-cycloalkyl,
(4) halo,
(5) $(C_1–C_4)$-perfluoroalkyl, or
(6) $R^4$ and $R^{4'}$ are taken together form a $(C_3–C_7)$-cycloalkyl ring;

Q is:
(1) $NR^5R^6$, wherein $R^5$ and $R^6$ are independently:
  (a) H,
  (b) $(C_1–C_4)$-perfluoroalkyl,
  (c) $(C_3–C_7)$-cycloalkyl,
  (d) $(C_2–C_6)$-alkyl-aryl, wherein aryl is defined as phenyl or naphthyl which is substituted with one, two or three of the substituents selected from the group consisting of halo, hydroxy, $(C_1–C_6)$-alkyl, $(C_1–C_4)$-perfluoroalkyl, $(C_1–C_6)$-alkoxy, phenyl, phenoxy, and nitro,
  (e) $(C_1–C_{10})$-alkyl, which is optionally substituted with one, two, or three of the substituents selected from the group consisting of:
    (a') halo, wherein halo is fluoro, chloro, bromo, or iodo,
    (b') hydroxy,
    (c') oxo,
    (d') $(C_1–C_6)$-alkoxy,
    (e') phenyl, and
    (f') $(C_3–C_7)$-cycloalkyl; or
  (f') optionally, $R^5$ or $R^6$ can be joined with the $R^2$ substituent in Formula I to form a 5 to 8 atom heterocyclic ring, and the other of $R^5$ or $R^6$ is as defined above;
(2) heterocyclyl, wherein heterocyclyl is defined as a monocyclic or bicyclic ring of 5 to 10 carbon atoms which can be aromatic or nonaromatic, wherein the heterocyclyl is attached to the methylene bearing the $R^4$ and $R^{4'}$ substituents through a N from the heterocyclyl and may optionally contain 1 to 3 additional heteroatoms selected from N, O or S and is optionally substituted with one, two, or three substituents selected from the group consisting of:
  (a) H,
  (b) $(C_1–C_6)$-alkyl,
  (c) $(C_1–C_4)$-perfluoroalkyl,
  (d) $(C_1–C_4)$-alkyl-aryl,
  (e) $CO_2(C_1–C_6)$-alkyl,
  (f) $CO_2H$
  (g) oxo, and
  (h) hydroxy; or
(3) $NH(C=O)R^7$, wherein $R^7$ is:
  (a) $(C_1–C_{13})$-alkyl or $(C_1–C_{12})$-alkenyl, which is optionally substituted with one, two, or three substituents selected from the group consisting of:
    (a') halo, wherein halo is fluoro, chloro, bromo, or iodo,
    (b') hydroxy,
    (c') oxo,
    (d') nitro,
    (e') $(C_1–C_6)$-alkoxy,
    (f') $NR^5R^6$,
    (g') $NH(CO)O(C_1–C_6)$-alkyl, wherein $(C_1–C_6$-alkyl is optionally substituted with phenyl,
    (h') $CO(C_1–C_{10})$-alkyl,
    (i') $OC(O)(C_1–C_6)$-alkyl, (j') (CONR⁵R⁶,
(k') O-aryl, wherein aryl as defined in (o') below,
(l') S-aryl, wherein aryl as defined in (o') below,
(m') ($C_3$–$C_7$)-cycloalkyl, which is optionally substituted with 1 to 3 substituents selected from the group consisting of ($C_1$–$C_6$)-alkoxy, CO($C_1$–$C_6$)-alkyl, oxo and ($C_1$–$C_6$)-alkyl optionally substituted with $NO_2$,
(n') ($C_1$–$C_7$)-cycloalkyl fused with phenyl, wherein ($C_5$–$C_7$)-cycloalkyl fused with phenyl is optionally substituted with 1 to 3 substituents selected from the group consisting of ($C_1$–$C_6$)-alkoxy, oxo, and ($C_1$–$C_6$)-alkyl,
(o') aryl, wherein aryl is defined as phenyl or naphthyl, which is optionally substituted with one, two or three of the substituents selected from the group consisting of:
  (a") halo, as defined above,
  (b") hydroxy,
  (c") ($C_1$–$C_6$)-alkyl,
  (d") ($C_1$–$C_4$)-perfluoroalkyl,
  (e") ($C_1$–$C_6$)-alkoxy, optionally substituted with phenyl,
  (f") phenyl,
  (g") phenoxy, and
  (h") nitro;
(p') heterocyclyl, wherein heterocyclyl is defined as a monocyclic, bicyclic, or tricyclic ring of 5 to 14 carbon atoms which can be aromatic or nonaromatic and containing from 1 to 3 heteroatoms selected from O, N or S, and the heterocyclyl being optionally substituted or with one, two, or three substituents selected from the group consisting of:
  (a") H,
  (b") halo, as defined above,
  (c") ($C_1$–$C_6$)-alkyl,
  (d") ($C_1$–$C_4$)-perfluoroalkyl,
  (e") ($C_1$–$C_4$)-alkyl-aryl,
  (f") ($C_1$–$C_6$)-alkoxy,
  (g") phenyl,
  (h") phenoxy,
  (i") nitro,
  (j") $CO_2$($C_1$–$C_6$)-alkyl, and
  (k") oxo; and
(q') S-heterocyclyl, wherein heterocyclyl as defined under
(p') above;
(b) aryl, wherein aryl is defined as phenyl or naphthyl which is optionally substituted with one, two or three of the substituents selected from the group consisting of:
  (a') halo, wherein halo is fluoro, chloro, bromo, or iodo,
  (b') ($C_1$–$C_6$)-alkyl,
  (c') ($C_1$–$C_6$)-alkoxy,
  (d') ($C_1$–$C_4$)-perfluoroalkyl;
  (e') phenoxy,
  (f') benzyl, and
  (g') phenyl optionally substituted with ($C_1$–$C_4$)-perfluoroalkyl;
(c) ($C_3$–$C_7$)-cycloalkyl, optionally substituted with phenyl; or
(d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of:
  (a') halo, as defined above,
  (b') ($C_1$–$C_6$)-alkyl,
  (c') ($C_1$–$C_4$)-perfluoroalkyl, and
  (d') ($C_1$–$C_6$)-alkoxy.

A preferred embodiment of the present invention is isoquinolinone compounds of structural Formula Ia:

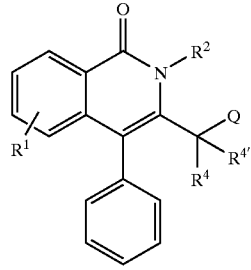

Ia or a pharmaceutically acceptable salts, hydrates, solvates, crystal forms, or stereoisomers thereof, wherein:
$R^1$ is:
  (1) ($C_1$–$C_6$)-alkoxy,
  (2) ($C_1$–$C_4$)-perfluoroalkyl,
  (3) ($C_1$–$C_4$)-perfluoroalkoxy, or
  (4) halo, wherein halo is fluoro, chloro, bromo, or iodo;
$R^2$ is:
  (1) ($C_1$–$C_6$)-alkyl,
  (2) $(CH_2)_n$—(T)$[S(O)_m]_p R^3$, or
  (3) $(CH_2)_n$—(T)$COR^3$;

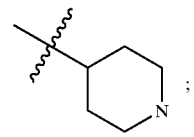

wherein T is —NH or
n is: 1, 2, or 3;
m is: 0, 1, or 2;
p is: 0, 1, or 1;
$R^3$ is:
  (1) aryl, wherein aryl is defined as phenyl or naphthyl which is optionally substituted with one, two or three of the substituents selected from the group consisting of:
    (a) halo, wherein halo is fluoro, chloro, bromo, or iodo,
    (b) ($C_1$–$C_6$)-alkyl,
    (c) ($C_1$–$C_6$)-alkoxy,
    (d) ($C_1$–$C_4$)-perfluoroalkyl,
    (e) ($C_1$–$C_4$)-perfluoroalkoxy,
    (f) phenyl, and
    (g) benzyl;
  (2) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of:
    (a) halo, as defined above,
    (b) ($C_1$–$C_6$)-alkyl,
    (c) ($C_1$–$C_4$)-perfluoroalkyl, and
    (d) ($C_1$–$C_6$)-alkoxy;
  (3) ($C_1$–$C_6$)-alkyl optionally substituted with phenyl; or
  (4) ($C_1$–$C_6$)-alkoxy;

$R^4$ and $R^{4'}$ are independently:
(1) H,
(2) $(C_1-C_4)$-alkyl,
(3) $(C_3-C_7)$-cycloalkyl,
(4) halo,
(5) $(C_1-C_4)$-perfluoroalkyl, or
(6) $R^4$ and $R^{4'}$ are taken together form a $(C_3-C_7)$-cycloalkyl ring;

Q is:
(1) $NR^5R^6$, wherein $R^5$ and $R^6$ are independently:
  (a) H,
  (b) $(C_1-C_4)$-perfluoroalkyl,
  (c) $(C_3-C_7)$-cycloalkyl,
  (d) $(C_2-C_6)$-alkyl-aryl, wherein aryl is defined as phenyl or naphthyl which is substituted with one, two or three of the substituents selected from the group consisting of halo, hydroxy, $(C_1-C_6)$-alkyl, $(C_1-C_4)$-perfluoroalkyl, $(C_1-C_6)$-alkoxy, phenyl, phenoxy, and nitro,
  (e) $(C_1-C_{10})$-alkyl, which is optionally substituted with one, two, or three of the substituents selected from the group consisting of:
    (a') halo, wherein halo is fluoro, chloro, bromo, or iodo,
    (b') hydroxy,
    (c') oxo,
    (d') $(C_1-C_6)$-alkoxy,
    (e') phenyl, and
    (f') $(C_3-C_7)$-cycloalkyl; or
  (f) optionally, $R^5$ or $R^6$ can be joined with the $R^2$ substituent in Formula Ia to form a 5 to 8 atom heterocyclic ring, and the other of $R^5$ or $R^6$ is as defined above;
(2) heterocyclyl, wherein heterocyclyl is defined as a monocyclic or bicyclic ring of 5 to 10 carbon atoms which can be aromatic or nonaromatic, wherein the heterocyclyl is attached to the methylene bearing the $R^4$ and $R^{4'}$ substituents through a N from the heterocyclyl and may optionally contain 1 to 3 additional heteroatoms selected from N, O or S and is optionally substituted with one, two, or three substituents selected from the group consisting of:
  (a) H,
  (b) $(C_1-C_6)$-alkyl,
  (c) $(C_1-C_4)$-perfluoroalkyl,
  (d) $(C_1-C_4)$-alkyl-aryl,
  (e) $CO_2(C_1-C_6)$-alkyl,
  (f) $CO_2H$
  (g) oxo, and
  (h) hydroxy; or
(3) $NH(C=O)R^7$, wherein $R^7$ is:
  (a) $(C_1-C_{13})$-alkyl or $(C_1-C_{12})$-alkenyl, which is optionally substituted with one, two, or three substituents selected from the group consisting of:
    (a') halo, wherein halo is fluoro, chloro, bromo, or iodo,
    (b') hydroxy,
    (c') oxo,
    (d') nitro,
    (e') $(C_1-C_6)$-alkoxy,
    (f") $NR^5R^6$,
    (g') $NH(CO)O(C_1-C_6)$-alkyl, wherein $(C_1-C_6)$-alkyl is optionally substituted with phenyl,
    (h') $CO(C_1-C_{10})$-alkyl,
    (i') $OC(O)(C_1-C_6)$-alkyl,
    (j') $CONR^5R^6$,
    (k') O-aryl, wherein aryl as defined in (o') below,
    (l') S-aryl, wherein aryl as defined in (o') below,
    (m') $(C_3-C_7)$-cycloalkyl, which is optionally substituted with 1 to 3 substituents selected from the group consisting of $(C_1-C_6)$-alkoxy, $CO(C_1-C_6)$-alkyl, oxo and $(C_1-C_6)$-alkyl optionally substituted with $NO_2$,
    (n') $(C_5-C_7)$-cycloalkyl fused with phenyl, wherein $(C_5-C_7)$-cycloalkyl fused with phenyl is optionally substituted with 1 to 3 substituents selected from the group consisting of $(C_1-C_6)$-alkoxy, oxo, and $(C_1-C_6)$-alkyl,
    (o') aryl, wherein aryl is defined as phenyl or naphthyl, which is optionally substituted with one, two or three of the substituents selected from the group consisting of:
      (a") halo, as defined above,
      (b") hydroxy,
      (c") $(C_1-C_6)$-alkyl,
      (d") $(C_1-C_4)$-perfluoroalkyl,
      (e") $(C_1-C_6)$-alkoxy, optionally substituted with phenyl,
      (f") phenyl,
      (g") phenoxy, and
      (h") nitro;
    (p') heterocyclyl, wherein heterocyclyl is defined as a monocyclic, bicyclic, or tricyclic ring of 5 to 14 carbon atoms which can be aromatic or nonaromatic and containing from 1 to 3 heteroatoms selected from O, N or S, and the heterocyclyl being optionally substituted or with one, two, or three substituents selected from the group consisting of:
      (a") H,
      (b") halo, as defined above,
      (c") $(C_1-C_6)$-alkyl,
      (d") $(C_1-C_4)$-perfluoroalkyl,
      (e") $(C_1-C_4)$-alkyl-aryl,
      (f") $(C_1-C_6)$-alkoxy,
      (g") phenyl,
      (h") phenoxy,
      (i") nitro,
      (j") $CO_2(C_1-C_6)$-alkyl, and
      (k") oxo; and
    (q') S-heterocyclyl, wherein heterocyclyl as defined under
    (p') above;
  (b) aryl, wherein aryl is defined as phenyl or naphthyl which is optionally substituted with one, two or three of the substituents selected from the group consisting of:
    (a') halo, wherein halo is fluoro, chloro, bromo, or iodo,
    (b') $(C_1-C_6)$-alkyl,
    (c') $(C_1-C_6)$-alkoxy,
    (d') $(C_1-C_4)$-perfluoroalkyl;
    (e') phenoxy,
    (f') benzyl, and
    (g') phenyl optionally substituted with $(C_1-C_4)$-perfluoroalkyl;
  (c) $(C_3-C_7)$-cycloalkyl, optionally substituted with phenyl; or
  (d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of:
    (a') halo, as defined above,
    (b') $(C_1-C_6)$-alkyl,
    (c') $(C_1-C_4)$-perfluoroalkyl, and
    (d') $(C_1-C_6)$-alkoxy.

Another preferred embodiment of the present invention is isoquinolinone compound of structural Formula Ib,

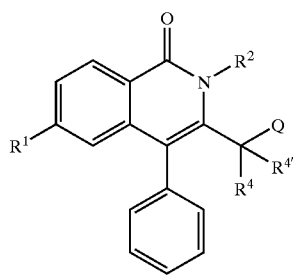

wherein the $R^1$, $R^2$, $R^4$, $R^{4'}$, and Q are as defined above.

Another preferred embodiment of the present invention is isoquinolinone compound of structural Formula Ic,

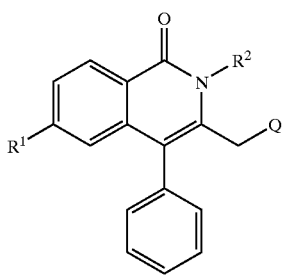

wherein $R^1$, $R^2$, and Q are as defined below:
$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;
$R^2$ is $(C_1-C_6)$-alkyl; and
Q is heterocyclyl which is selected from the group consisting of: pyrrolidinyl, piperazinyl, imidazolyl, morpholinyl, 1,4-dioxa-8-aza-spiro[4,5]decyl, piperidinyl, and 2,3-dihydroindolyl and the heterocyclyl is optionally substituted with one, two, or three substituents selected from the group consisting of H, $(C_1-C_4)$-alkyl, $CF_3$, benzyl, and $CO_2Et$.

Another preferred embodiment of the present invention is isoquinolinone compound of structural Formula Id,

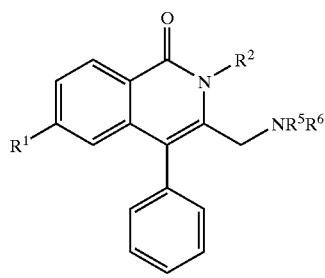

wherein $R^1$, $R^2$, $R^5$ and $R^6$ are as defined below:
$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;
$R^2$ is $(C_1-C_6)$-alkyl; and
$R^5$ and $R^6$ are independently: $(C_1-C_{10})$-alkyl optionally substituted with $(C_3-C_7)$-cycloalkyl, $(C_1-C_4)$-perfluoroalkyl, and phenyl.

Another preferred embodiment of the present invention is isoquinolinone compound of structural Formula Ie,

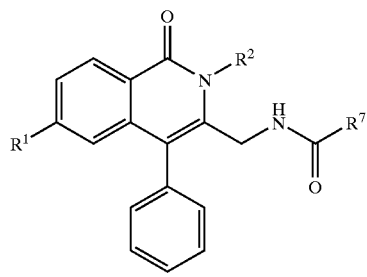

wherein $R^1$, $R^2$ and $R^7$ are as defined below:
$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;
$R^2$ is $(C_1-C_6)$-alkyl; and
$R^7$ is:
(a) $(C_1-C_{13})$-alkyl or $(C_1-C_{12})$-alkenyl, which is optionally substituted with one, two, or three substituents selected from the group consisting of:
(a') hydroxy,
(b') oxo,
(c') $NR^5R^6$,
(d') $NH(CO)O(C_1-C_6)$-alkyl, wherein $(C_1-C_6)$-alkyl optionally substituted with phenyl,
(e') $CO(C_1-C_{10})$-alkyl,
(f') $OC(O)(C_1-C_6)$-alkyl,
(g') $CONR^5R^6$,
(h') O-aryl, wherein aryl as defined in (l') below,
(i') S-aryl, wherein aryl as defined in (l') below,
(j') $(C_3-C_7)$-cycloalkyl, which is optionally substituted with 1 to 3 substituents selected from the group consisting of $(C_1-C_6)$-alkoxy, $CO(C_1-C_6)$-alkyl, and oxo, and $(C_1-C_6)$-alkyl optionally substituted with $NO_2$,
(k') $(C_5-C_7)$-cycloalkyl fused with phenyl, wherein $(C_5-C_7)$-cycloalkyl fused with phenyl is optionally substituted with 1 to 3 substituents selected from the group consisting of $(C_1-C_6)$-alkoxy, oxo, and $(C_1-C_6)$-alkyl,
(l') aryl, wherein aryl is defined as phenyl or naphthyl, which is optionally substituted with one, two or three of the substituents selected from the group consisting of:
(a") halo, as defined above,
(b") hydroxy,
(c") $(C_1-C_6)$-alkyl,
(d") $(C_1-C_4)$-perfluoroalkyl,
(e") $(C_1-C_6)$-alkoxy, optionally substituted with phenyl
(f") phenyl,
(g") phenoxy, and
(h") nitro;
(m') heterocyclyl, wherein heterocyclyl is defined as a monocyclic, bicyclic, or tricyclic ring of 5 to 14 carbon atoms which can be aromatic or nonaromatic and containing from 1 to 3 heteroatoms selected from O, N or S, and the heterocyclyl being optionally substituted or with one two, or three substituents selected from the group consisting of:
(a") H,
(b") halo, as defined above,
(c") $(C_1-C_6)$-alkyl, (d") $(C_1-C_4)$-perfluoroalkyl,
(e") $(C_1-C_4)$-alkyl-aryl,
(f") $(C_1-C_6)$-alkoxy,
(g") phenyl,
(h") phenoxy,
(i") nitro,
(j") $CO_2(C_1-C_6)$-alkyl, and
(k") oxo; and
(n') S-heterocyclyl, wherein heterocyclyl as defined under (m') above;
(b) aryl, wherein aryl is defined as phenyl or naphthyl which is optionally substituted with one, two or three of the substituents selected from the group consisting of:
(a') halo, wherein halo is fluoro, chloro, bromo, or iodo,
(b') $(C_1-C_6)$-alkoxy,
(c') phenoxy,
(d') benzyl, and
(e') phenyl optionally substituted with $(C_1-C_4)$-perfluoroalkyl;
(c) $(C_3-C_7)$-cycloalkyl, optionally substituted with phenyl; or
(d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of:
(a') halo, as defined above,
(b') $(C_1-C_6)$-alkyl,
(c') $(C_1-C_4)$-perfluoroalkyl, and
(d') $(C_1-C_6)$-alkoxy.

Another preferred embodiment of the present invention is isoquinolinone compound of structural Formula If,

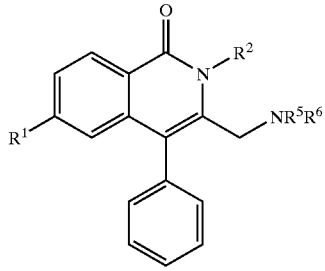

If wherein $R^1$, $R^2$, $R^3$, $R^5$, $R^6$, and n are as defined below:
$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;
$R^2$ is $(CH_2)_n(T)SO_2R^3$ or $(CH_2)_n(T)COR^3$,
$R^3$ is:
(a) $(C_1-C_6)$-alkyl optionally substituted with phenyl;
(b) phenyl or naphthyl optionally substituted with one, two, or three substituents selected from the group consisting of $OCF_3$, $O(CH_3)_3$, $CH_3$, $CF_3$ and halo;
(c) $(C_1-C_6)$-alkoxy; and
(d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of $(C_1-C_6)$-alkyl and $(C_1-C_6)$-alkoxy;
$R^5$ and $R^6$ are independently:
(a) $(C_1-C_4)$-perfluoroalkyl,
(b) phenyl, and
(c) $(C_1-C_{10})$-alkyl optionally substituted with $(C_3-C_7)$-cycloalkyl; and
n is 1, 2, or 3.

Another preferred embodiment of the present invention is isoquinolinone compound of structural Formula Ig,

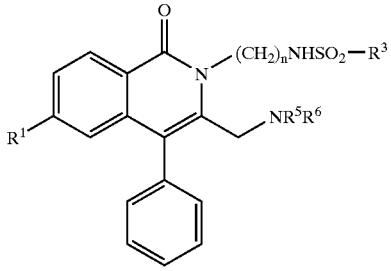

Ig wherein $R^1$, $R^3$, $R^5$, and $R^6$, and n are as defined below:
$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;
$R^3$ is:
(a) $(C_1-C_6)$-alkyl optionally substituted with phenyl;
(b) phenyl or naphthyl optionally substituted with one, two, or three substituents selected from the group consisting of $OCF_3$, $O(CH_3)_3$, $CH_3$, $CF_3$ and halo;
(c) $(C_1-C_6)$-alkoxy; and
(d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents of $(C_1-C_6)$-alkyl;
$R^5$ and $R^6$ are independently:
(a) $(C_1-C_4)$-perfluoroalkyl,
(b) phenyl, and
(c) $(C_1-C_{10})$-alkyl optionally substituted with $(C_3-C_7)$-cycloalkyl; and
n is 1, 2, or 3.

The compound of the present invention includes, but is not limited to: 3-dimethylaminomethyl-6-methoxy-2-methyl-4-phenyl-2H-isoquinolin-1-one;
3-(2,3-dihydro-indol-1-ylmethyl)-6-methoxy-2-methyl-4-phenyl-2H-isoquinolin-1-one;
3-[(ethyl-methyl-amino)-methyl]-6-methoxy-2-methyl-4-phenyl-2H-isoquinolin-1-one;
6-methoxy-2-methyl-4-phenyl-3-piperidin-1-ylmethyl-2H-isoquinolin-1-one;
3-[(tert-butyl-methyl-amino)-methyl]-6-methoxy-2-methyl-4-phenyl-2H-isoquinolin-1-one;
3-[(isopropyl-methyl-amino)-methyl]-6-methoxy-2-methyl-4-phenyl-2H-isoquinolin-1-one;
3-[(isopropyl-methyl-amino)-methyl]-6-methoxy-2-methyl-4-phenyl-2H-isoquinolin-1-one;
6-methoxy-2-methyl-4-phenyl-3-[(2,2,2-trifluoro-ethylamino)-methyl]-2H-isoquinolin-1-one;
2-(5-methoxy-2-methyl-1H-indol-3-yl)-N-(6-methoxy-2-methyl-1-oxo-4-phenyl-1,2-dihydro-isoquinolin-3-ylmethyl)-acetamide;
N-[2-(3-dimethylaminomethyl-6-methoxy-1-oxo-4-phenyl-1H-isoquinolin-2-yl)-ethyl]-methanesulfonamide;
butane-1-sulfonic acid [2-(3-dimethylaminomethyl-6-methoxy-1-oxo-4-phenyl-1H-isoquinolin-2-yl)-ethyl]-amide;
thiophene-2-sulfonic acid [2-(3-dimethylaminomethyl-6-methoxy-1-oxo-4-phenyl-1H-isoquinolin-2-yl)-ethyl]-amide;
N-[2-(3-dimethylaminomethyl-6-methoxy-1-oxo-4-phenyl-1H-isoquinolin-2-yl)-ethyl]-benzenesulfonamide;

furan-2-carboxylic acid [2-(3-dimethylaminomethyl-6-methoxy-1-oxo-4-phenyl-1H-isoquinolin-2-yl)-ethyl]-amide;

N-[2-(3-dimethylaminomethyl-6-methoxy-1-oxo-4-phenyl-1H-isoquinolin-2-yl)-ethyl]-2-phenyl-acetamide hydrochloride;

N-[2-(3-dimethylaminomethyl-6-methoxy-1-oxo-4-phenyl-1H-isoquinolin-2-yl)-ethyl]-nicotinamide;

9-methoxy-2-methyl-11-phenyl-1,2,3,4-tetrahydro-pyrazino[1,2-b]isoquinolin-6-one;

2-(1-acetyl-piperidin-4-ylmethyl)-3-dimethylaminomethyl-6-methoxy-4-phenyl-2H-isoquinolin-1-one;

3-dimethylaminomethyl-2-(1-methanesulfonyl-piperidin-4-ylmethyl)-6-methoxy-4-phenyl-2H-isoquinolin-1-one;

[2-(3-dimethylaminomethyl-6-methoxy-1-oxo-4-phenyl-1H-isoquinolin-2-yl)-ethyl]-carbamic acid tert-butyl ester;

N-[2-(3-dimethylaminomethyl-6-methoxy-1-oxo-4-phenyl-1H-isoquinolin-2-yl)-ethyl]-isonicotinamide; and

[2-(3-aminomethyl-6-methoxy-1-oxo-4-phenyl-1H-isoquinolin-2-yl)-ethyl]-carbamic acid tert-butyl ester.

A preferred compound is a 3-dimethylaminomethyl-6-methoxy-2-methyl-4-phenyl-2H-isoquinolin-1-one or a pharmaceutically acceptable salt, hydrate, solvate, crystal form, or stereoisomer thereof as shown below:

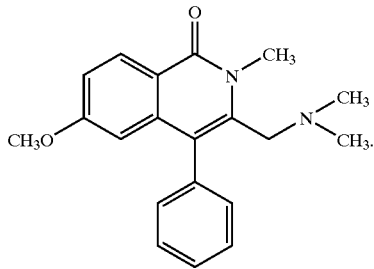

Also encompassed by the present invention is a method of treating a condition in a mammal, the treatment of which is effected or facilitated by $K_v1.5$ inhibition or potassium current, $I_{Kur}$, comprising the administration of a therapeutically effective amount of the compound of Formula I as recited above.

Another embodiment of the present invention is a method of treating a condition in a mammal, the treatment of which is effected or facilitated by $K_v1.5$ inhibition or $I_{Kur}$ current inhibition, comprising the administration of a therapeutically effective amount of pharmaceutical composition which comprises a pharmaceutical carrier and a compound of Formula I as recited above.

A preferred embodiment of the present invention is a method of preventing or treating atrial arrhythmias in a mammal, comprising the administration of a therapeutically effective amount of the compound of Formula I as recited above.

A more preferred embodiment of the present invention is a method of preventing or treating atrial arrhythmias in a mammal comprising a therapeutically effective amount of 3-dimethylaminomethyl-6-methoxy-2-methyl-4-phenyl-2H-isoquinolin-1-one or a pharmaceutically acceptable salt, hydrate, solvate, crystal form, and stereoisomer thereof.

The present invention also includes a pharmaceutical composition for the treatment of an atrial arrhythmia, comprising a pharmaceutically acceptable carrier and at least one compound of Formula I or its pharmaceutically acceptable salt, hydrate, solvate, crystal form, and stereoisomer thereof.

The present invention further includes a process for making a pharmaceutical composition comprising a compound of Formula I or its pharmaceutically acceptable salt, hydrate, solvate, crystal form, and stereoisomer thereof and a pharmaceutically acceptable carrier.

The compounds of the present invention include all of the pharmaceutically acceptable salts, hydrates, solvates, crystal forms, and stereoisomers of a compound of Formula I.

As used herein, the term "alkyl," unless otherwise indicated, includes those alkyl groups of a designated number of carbon atoms of either a straight, branched, or cyclic configuration. Examples of "alkyl" include methyl, ethyl, propyl, isopropyl, butyl, sec-butyl, tert-butyl, pentyl, hexyl, heptyl, and the like. Examples of cycloalkyls are cyclopropyl, cyclobutyl, cyclopentyl, cyclohexyl, cycloheptyl, norbornyl, 1,1,3,3-tetramethyl butyl, and the like.

The term "alkenyl" includes hydrocarbon chains of a specified number of carbon atoms of either a straight or branched configuration and at least one unsaturation, which may occur at any point along the chain, such as ethenyl, propenyl, butenyl, pentenyl, and the like.

Alkyl, cycloalkyl, and alkenyl can be optionally substituted with one, two, or three substituents as set forth in the embodiments recited above.

The term "aryl," unless specifically defined otherwise, is defined as phenyl or naphthyl which may be optionally substituted with one, two or three of the substituents as set forth in the embodiments recited above.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like.

The term "heteroaryl" as utilized herein, unless specifically defined otherwise, is intended to include a monocyclic or bicyclic (fused) aromatic ring of 5 to 10 carbon atoms containing from 1 to 3 heteroatoms selected from O, N and/or S, and the heterocyclyl being optionally substituted with one, two, or three substituents as set forth in the embodiments recited above. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

The term $NR^5R^6$ in Q substituent means an amino group wherein $R^5$ and $R^6$ are independently selected from the group as set forth in the embodiments recited above. Optionally $R^5$ or $R^6$ can be joined with $R^2$ substituent in Formula I to form a 5 to 8 atom heterocyclic ring, and the other of $R^5$ or $R^{\neq}$ is defined in the embodiment recited above.

"Heterocyclyl," unless specifically defined otherwise, is defined as a monocyclic or bicyclic ring of 5 to 14 carbon atoms which can be aromatic or nonaromatic, and may contain 1 to 4 heteroatoms selected from N, O, and S, which is optionally substituted with one, two, or three substituents as set forth in the embodiments recited above.

When Q is defined as $NH(C=O)R^7$ and $R^7$ is defined as set forth in the embodiments recited above.

The heterocyclyl groups within the scope of this definition include but are not limited to: pyrrolidinyl, piperazinyl, morpholinyl, 1,4-dioxa-8-aza-spiro[4,5]decyl, peperidinyl, 2,3-dihydroindolyl, indolyl, dithiolanyl, oxo-hexahydrothieno[3,4-d]imidazolyl, thiophenyl, benzoimidazol, dioxo-2,5-dihydro-pyrrolyl, 6-methoxy-3-oxo-ndanyl, 6-chloro-9H-carbazoyl, 5-fluoro-1H-indolyl, quinoxalinyl, 5-methoxy-2-methyl-1H-indolyl, thiophene, 1-methyl-1H-imidazol, 3,5-dimethyl-isoxazole, quinoline, furan, 1,2,3,4-tetrahydro-pyrazino, and piperidinyl.

In the compounds of Formula I, the heteroaryl, heterocyclyl or aryl groups may be optionally substituted with the substituents listed above at any available carbon atom or heteroatom. The heterocyclyl may also be spiro or fused to a second 5-, 6-, or 7-membered ring containing one or two oxygens such as: dioxolanyl, dihydrofuranyl, dihydropyranyl, and dioxanyl. Disubstituted aryl groups may be ortho, para or meta and all three are intended unless specifically defined otherwise.

Pharmaceutically acceptable salts include both the metallic (inorganic) salts and organic salts; a list of which is given in *Remington's Pharmaceutical Sciences,* 17th Edition, p.1418 (1985). It is well known to one skilled in the art that an appropriate salt form is chosen based on physical and chemical stability, flowability, hydgroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Also included within the scope of this invention are crystal forms, hydrates and solvates of the compounds of Formula I.

The term aprotic solvent means a type of solvent which neither donates nor accepts protons. An aprotic solvent includes, but is not limited to: tetrahydrofuran (THF), acetonitrile, dimethylformamide (DMF), dimethylacetamide (DMA), N-methylpyrrolidinone (NMP), diethyl ether, dichloromethane, chloroform, ethyl acetate, pentane, hexane, toluene, benzene, chlorobenzene, methyl tert-butyl ether (MTBE) and mixtures thereof.

The term "treating" as used herein refers to the management and care of a mammal afflicted with a condition or disorder for which the administration of a compound in accordance with the present invention alters the action or activity of a potassium channel or potassium current to prevent the onset of symptoms or complications caused by the condition or disorder, or to eliminate the condition or disorder altogether.

For the purpose of this disclosure, a mammal is a member of the animal kingdom possessed of a homeostatic mechanism which includes human and birds.

The dosage administered will be dependent on the age, health and weight of the recipient, the extent of disease, kind of concurrent treatment, if any, frequency of treatment and the nature of the effect desired. In the method of treating arrhythmia of the present invention, a compound or pharmaceutically acceptable salt thereof, is administered in an amount ranging from about 0.01 to about 50 mg per kg of body weight per day, preferably from about 0.10 to about 30 mg per kg of body weight per day in a single dose or in 2 to 4 divided doses.

The compounds of the present invention can be administered as the sole active ingredient or in combination with other antiarrhythmic agents or other cardiovascular agents such as but are not limited to ACE inhibitors, angiotensin II antagoinst, selective and nonselective beta blockers, endothelin antagonist, thrombin inhibitors, aspierin, warfarin, and factor Xa inhibitors. The compounds, or pharmaceutically acceptable salts thereof, of the present invention, in the described dosages, are administered orally, intraperitoneally, subcutaneously, intramuscularly, transdermally, sublingually or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

Methods for preparing the compounds of the present invention are illustrated in the following schemes and examples. Other synthetic routes would be readily apparent to those skilled in the art.

REACTION SCHEME A

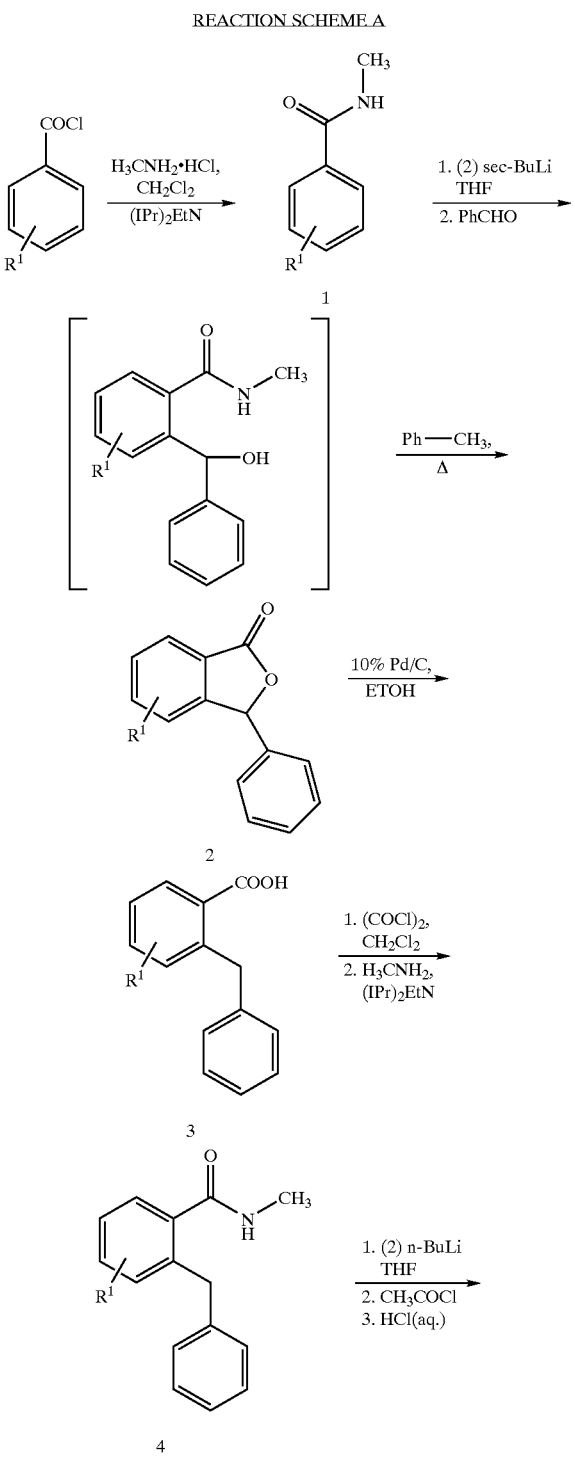

-continued

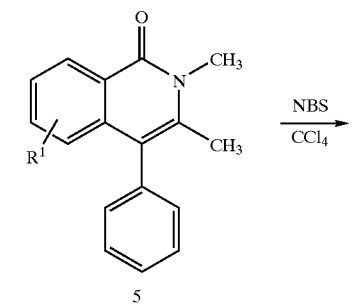

5

NBS / CCl4 →

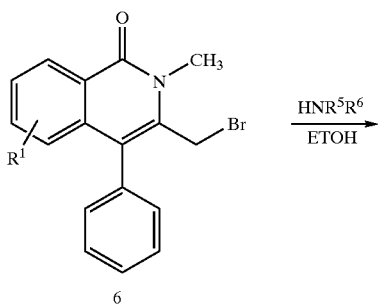

6

HNR⁵R⁶ / ETOH →

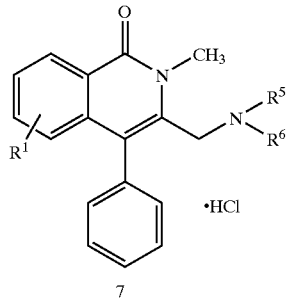

7 ·HCl

In Reaction Scheme A, treatment of anisoyl chloride with methylamine hydrochloride and diisopropylethylamine in aprotic organic solvent gave amide (1). Reaction with a base in aprotic solvent followed by addition of benzaldehyde afforded alcohol. Refluxing in toluene gave the lactone (2) which was then converted to the carboxylic acid (3) by catalytic hydrogenation. Treatment of the acid (3) with oxalyl chloride followed by reaction with methylamine gave the N-methylamide (4). The dianion of the compound (4) was prepared by using a base, and reaction with acetyl chloride gave the key intermediate cyclized product (5), which was further halogenated to give bromomethyl compound (6). The nucleophlilic displacement of halogen with an amine afforded the final product if aminomethyl compound (7).

Table 1 below provides the compounds that were prepared in accordance with Reaction Scheme A.

TABLE 1

Reaction of 15 With HNR⁵R⁶ to Compounds Give Compounds 14 and 16–38

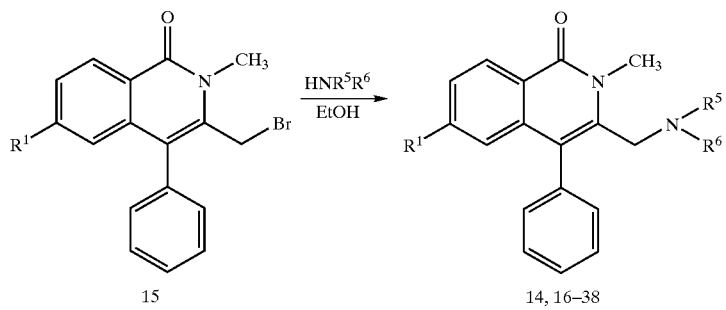

| NO. | Compound Name | R¹ | HNR⁵R⁶ | MS [M + H]⁺ | Salt Form |
|---|---|---|---|---|---|
| 14 | 3-Dimethylaminomethyl-6-methoxy-2-methyl-4-phenyl-2H-isoquinolin-1-one | OCH₃ | HN(CH₃)₂ | 323 | .HCl |
| 16 | 2-Methyl-4-phenyl-3-pyrrolidin-1-ylmethyl-2H-isoquinolin-1-one | H | pyrrolidine | 319.2 | free base |
| 17 | 3-(Isobutylamino-methyl)-2-methyl-4-phenyl-2H-isoquinalin-1-one | H | H₂N-CH₂CH(CH₃)₂ | 321.2 | free base |
| 18 | 3-[(3-Methoxy-propylamino)-methyl]-2-methyl-4-phenyl-2H-isoquinolin-1-one | H | H₂N(CH₂)₃OCH₃ | 337.2 | .HCl |
| 19 | 2-Methyl-3-(4-methyl-piperazin-1-ylmethyl)-4-phenyl-2H-isoquinolin-1-one | H | 4-methylpiperazine | 348.2 | free base |

TABLE 1-continued

Reaction of 15 With HNR⁵R⁶ to Compounds
Give Compounds 14 and 16–38

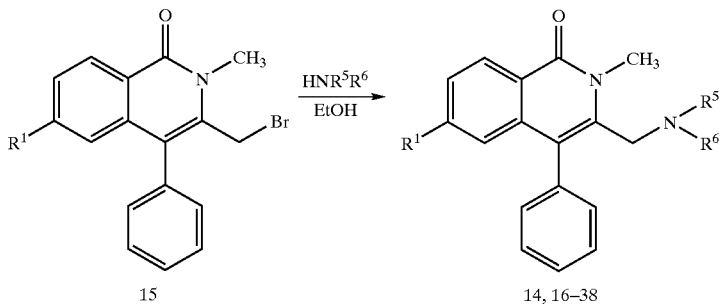

| NO. | Compound Name | R¹ | HNR⁵R⁶ | MS [M + H]⁺ | Salt Form |
|---|---|---|---|---|---|
| 20 | 3-Imidazol-1-ylmethyl-2-methyl-4-phenyl-2H-isoquinolin-1-one | H | imidazole | 312.2 | free base |
| 21 | 2-Methyl-3-morpholin-4-ylmethyl-4-phenyl-2H-isoquinolin-1-one | H | morpholine | 335 | free base |
| 22 | 3-(1,4-Dioxa-8-aza-spiro[4.5]dec-8-ylmethyl)-2-methyl-4-phenyl-2H-isoquinolin-1-one | H | 1,4-dioxa-8-azaspiro[4.5]decane | 391 | free base |
| 23 | 2-Methyl-4-phenyl-3-piperidin-1-ylmethyl-2H-isoquinolin-1-one | H | piperidine | 333 | free base |
| 24 | 6-Methoxy-2-methyl-3-(4-methyl-piperidin-1-ylmethyl)-4-phenyl-2H-isoquinolin-1-one | OCH₃ | 4-methylpiperidine | 377 | free base |
| 25 | 1-(6-Methoxy-2-methyl-1-oxo-4-phenyl-1,2-dihydro-isoquinolin-3-ylmethyl)-piperidine-4-carboxylic acid | OCH₃ | ethyl piperidine-4-carboxylate | 435 | .HCl |
| 26 | 3-(2,3-Dihydro-indol-1-ylmethyl)-6-methoxy-2-methyl-4-phenyl-2H-isoquinolin-1-one | OCH₃ | 2,3-dihydroindole | 397 | free base |
| 27 | 3-(4-Benzyl-piperidin-1-ylmethyl)-6-methoxy-2-methyl-4-phenyl-2H-isoquinolin-1-one | OCH₃ | 4-benzylpiperidine | 453 | .HCl |

TABLE 1-continued

Reaction of 15 With HNR⁵R⁶ to Compounds Give Compounds 14 and 16–38

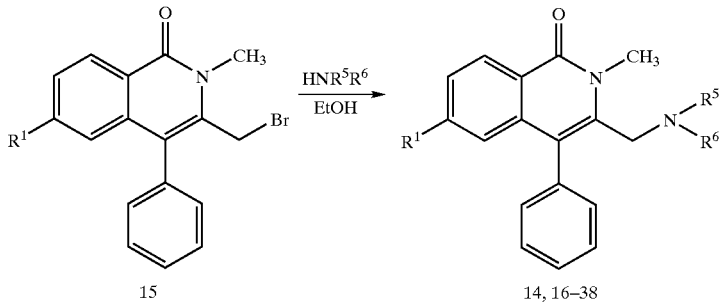

| NO. | Compound Name | R$^1$ | HNR$^5$R$^6$ | MS [M + H]$^+$ | Salt Form |
|---|---|---|---|---|---|
| 28 | 6-Methoxy-2-methyl-4-phenyl-3-piperidin-1-ylmethyl-2H-isoquinolin-1-one | OCH$_3$ | | 363 | free base |
| 29 | 3-[(Diisopropylamino)-methyl]-6-methoxy-2-methyl-4-phenyl-2H-isoquinolin-1-one | OCH$_3$ | | 379.2 | free base |
| 30 | 3-[(tert-Butyl-methyl-amino)-methyl]-6-methoxy-2-methyl-4-phenyl-2H-isoquinolin-1-one | OCH$_3$ | | 365.34 | free base |
| 31 | 3-[(Cyclopropylmethyl-propyl-amino)-methyl]-6-methoxy-2-methyl-4-phenyl-2H-isoquinolin-1-one | OCH$_3$ | | 391 | free base |
| 32 | 3-[(Ethyl-methyl-amino)-methyl]-6-methoxy-2-methyl-4-phenyl-2H-isoquinolin-1-one | OCH$_3$ | | 337.32 | free base |
| 33 | 6-Methoxy-2-methyl-3-methylaminomethyl-4-phenyl-2H-isoquinolin-1-one | OCH$_3$ | H$_2$N— | 309.31 | free base |
| 34 | 3-[Isopropyl-methyl-amino)-methyl]-6-methoxy-2-methyl-4-phenyl-2H-isoquinolin-1-one | OCH$_3$ | | 351.34 | free base |
| 35 | 3-(2,6-Dimethyl-piperidin-1-ylmethyl)-6-methoxy-2-methyl-4-phenyl-2H-isoquinolin-1-one | OCH$_3$ | | 391.2 | free base |

TABLE 1-continued

Reaction of 15 With HNR⁵R⁶ to Compounds Give Compounds 14 and 16–38

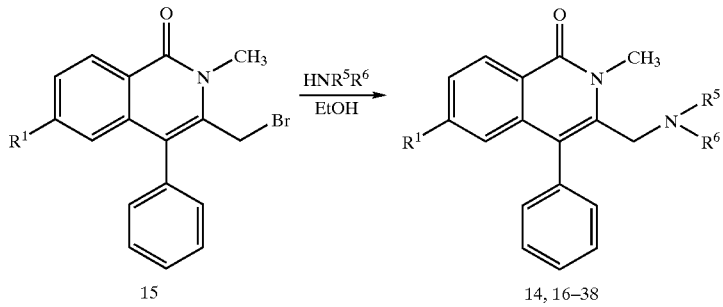

| NO. | Compound Name | $R^1$ | $HNR^5R^6$ | MS $[M + H]^+$ | Salt Form |
|---|---|---|---|---|---|
| 36 | 6-Methoxy-2-methyl-4-phenyl-3-[(1,1,3,3-tetramethyl-butylamino)-methyl]-2H-isoquinolin-1-one | $OCH_3$ | | 407.2 | free base |
| 37 | 6-Methoxy-2-methyl-3-[(1-methyl-1-phenyl-ethylamino)-methyl]-4-phenyl 2H-isoquinolin-1-one | $OCH_3$ | | 413.1 | free base |
| 38 | 6-Methoxy-2-methyl-4-phenyl-3-[(2,2,2-trifluoro-ethylamino)-methyl]-2H-isoquinolin-1-one | $OCH_3$ | | 377.2 | .HCl |

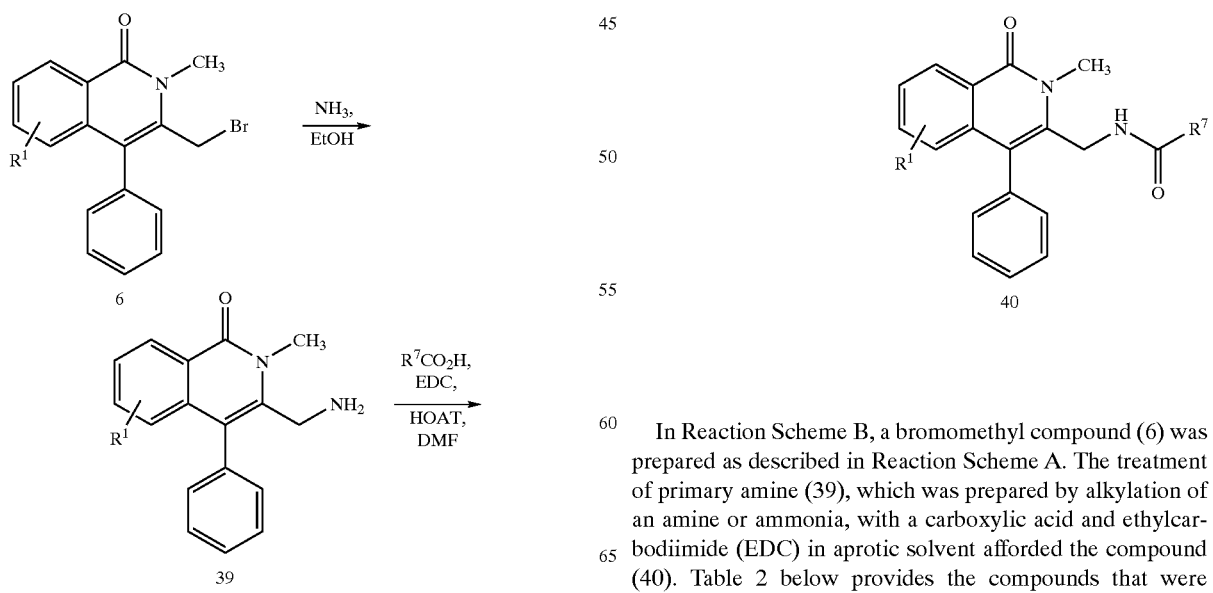

In Reaction Scheme B, a bromomethyl compound (6) was prepared as described in Reaction Scheme A. The treatment of primary amine (39), which was prepared by alkylation of an amine or ammonia, with a carboxylic acid and ethylcarbodiimide (EDC) in aprotic solvent afforded the compound (40). Table 2 below provides the compounds that were prepared in accordance with Reaction Scheme B.

TABLE 2

Reaction of 41 With Carboxylic Acids to Give Compunds 42–97

| No. | Compound Name | R⁷CO₂H | MS [M + H] | Salt Form |
|---|---|---|---|---|
| 42 | 5-Phenyl-pentanoic acid (6-methoxy-2-methyl-1-oxo-4-phenyl-1,2-dihydro-isoquinolin-3-ylmethyl)-amide | | 455.4 | free base |
| 43 | N-(6-Methoxy-2-methyl-1-oxo-4-phenyl-1,2-dihydro-isoquinolin-3-ylmethyl)-3-o-tolyl-propionamide | | 441.3 | free base |
| 44 | 3-(R)-7-Dimethyl-oct-6-enoic acid (6-methoxy-2-methyl-1-oxo-4-phenyl-1,2-dihydro-isoquinolin-3-ylmethyl)-amide | | 447.3 | free base |
| 45 | N-(6-Methoxy-2-methyl-1-oxo-4-phenyl-1,2-dihydro-isoquinolin-3-ylmethyl)-2-(2-methyl-1H-indol-3-ylmethyl)-acetamide | | 345.3 | free base |
| 46 | 5-[1,2]Dithiolan-3-yl-pentanoic acid (6-methoxy-2-methyl-1-oxo-4-phenyl-1,2-dihydro-isoquinolin-3-ylmethyl)-amide | | 483.3 | free base |
| 47 | N-(6-Methoxy-2-methyl-1-oxo-4-phenyl-1,2-dihydro-isoquinolin-3-ylmethyl)-2-[(1R)-(2S)-(3R)]-(3-methyl-2-nitromethyl-5-oxo-cyclopentyl)-acetamide | | 492.3 | free base |
| 48 | 5-(2-Oxo-hexahydro-thieno[3,4-d]imidazol-6-yl)-pentanoic acid (6-methoxy-2-methyl-1-oxo-4-phenyl-1,2-dihydro-isoquinolin-3-ylmethyl)-amide | | 521.4 | free base |
| 49 | N-(6-Methoxy-2-methyl-1-oxo-4-phenyl-1,2-dihydro-isoquinolin-3-ylmethyl)-4-thiophen-2-yl-butyramide | | 447.3 | free base |
| 50 | Pent-4-enoic acid (6-methoxy-2-methyl-1-oxo-4-phenyl-1,2-dihydro-isoquinolin-3-ylmethyl)-amide | | 377.3 | free base |

TABLE 2-continued

Reaction of 41 With Carboxylic Acids to Give Compounds 42–97

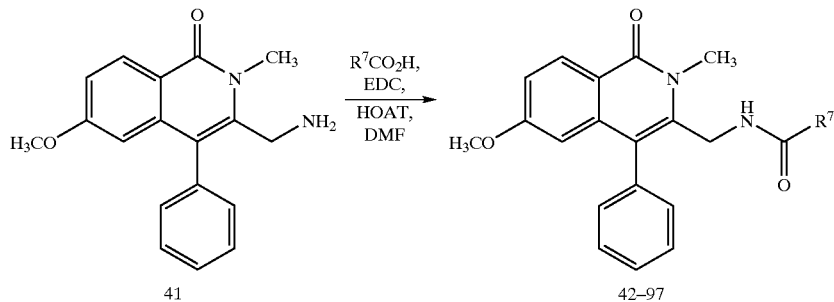

| No. | Compound Name | $R^7CO_2H$ | MS [M + H] | Salt Form |
|---|---|---|---|---|
| 51 | (5-[(6-Methoxy-2-methyl-1-oxo-4-phenyl-1,2-dihydro-isoquinolin-3-ylmethyl)-carbamoyl]-pentyl)carbamic acid phenethyl ester | | 542.4 | free base |
| 52 | N-(6-Methoxy-2-methyl-1-oxo-4-phenyl-1,2-dihydro-isoquinolin-3-ylmethyl)-2-(2-trifluoromethyl-phenyl)-acetamide | | 481.3 | free base |
| 53 | 4-Phenyl-but-3-enoic acid (6-methoxy-2-methyl-1-oxo-4-phenyl-1,2-dihydro-isoquinolin-3-ylmethyl)-amide | | 439.3 | free base |
| 54 | N-(6-Methoxy-2-methyl-1-oxo-4-phenyl-1,2-dihydro-isoquinolin-3-ylmethyl)-3-(3,4,5-trimethoxy-phenyl)-propionamide | | 517.5 | free base |
| 55 | Tetradecanoic acid (6-methoxy-2-methyl-1-oxo-4-phenyl-1,2-dihydro-isoquinolin 3-ylmethyl)-amide | | 505.6 | free base |
| 56 | N-(6-Methoxy-2-methyl-1-oxo-4-phenyl-1,2-dihydro-isoquinolin-3-ylmethyl)-3-nitro-propionamide | | 396.3 | free base |
| 57 | 3-(1H-Benzoimidazol-2-yl)-N-(6-methoxy-2-methyl-1-oxo-4-phenyl-1,2-dihydro-isoquinolin-3-ylmethyl)-propionamide | | 467.4 | free base |
| 58 | 4-(3,4-Dimethoxy-phenyl)-N-(6-methoxy-2-methyl-1-oxo-4-phenyl-1,2-dihydro-isoquinolin-3-ylmethyl)-butyramide | | 501.5 | free base |
| 59 | 3-(2,5-Dioxo-2,5-dihydro-pyrrol-1-yl)-N-(6-methoxy-2-methyl-1-oxo-4-phenyl-1,2-dihydro-isoquinolin-3-ylmethyl)-propionamide | | 446.3 | free base |

TABLE 2-continued

Reaction of 41 With Carboxylic Acids to Give Compounds 42–97

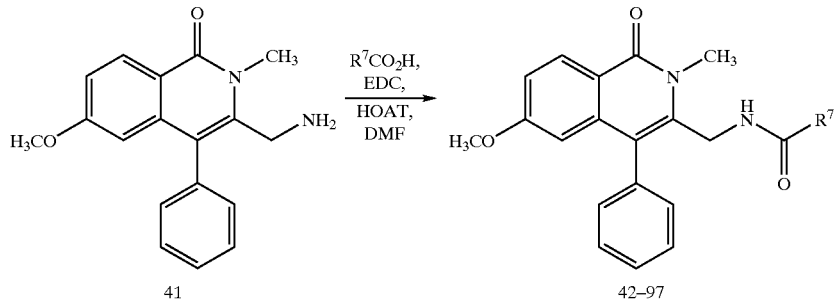

| No. | Compound Name | R⁷CO₂H | MS [M + H] | Salt Form |
|---|---|---|---|---|
| 60 | N-(6-Methoxy-2-methyl-1-oxo-4-phenyl-1,2-dihydro-isoquinolin-3-ylmethyl-3-(3-methoxy-phenyl-propionamide | HO₂C–CH₂CH₂–C₆H₄–OCH₃ | 457.4 | free base |
| 61 | Diethylamino-N-(6-methoxy-2-methyl-1-oxo-4-phenyl-1,2-dihydro-isoquinolin-3-ylmethyl)-propionamide | HO₂C–CH₂CH₂–N(Et)₂ | 422.4 | free base |
| 62 | Dimethylamino-N-(6-methoxy-2-methyl-1-oxo-4-phenyl-1,2-dihydro-isoquinolin-3-ylmethyl)-butyramide | HO₂C–(CH₂)₃–N(Me)₂ | 408.4 | free base |
| 63 | 4-(2,4-Dichloro-phenoxy)-N-(6-methoxy-2-methyl-1-oxo-4-phenyl-1,2-dihydro-isoquinolin-3-ylmethyl)-butyramide | HO₂C–(CH₂)₃–O–C₆H₃(2,4-Cl₂) | 525.4 | free base |
| 64 | 4,4-Bis-(4-hydroxy-phenyl)-pentanoic acid (6-methoxy-2-methyl-1-oxo-4-phenyl-1,2-dihydro-isoquinolin-3ylmethyl)-amide | HO₂C–CH₂CH₂–C(CH₃)(4-HydroxyPh)₂ | 563.3 | free base |
| 65 | 4-Cyclohexyl-N-(6-methoxy-2-methyl-1-oxo-4-phenyl-1,2-dihydro-isoquinolin-3-ylmethyl)-butyramide | HO₂C–(CH₂)₃–cyclohexyl | 447.4 | free base |
| 66 | N-(6-Methoxy-2-methyl-1-oxo-4-phenyl-1,2-dihydro-isoquinolin-3-ylmethyl)-3-p-tolylsulfanyl-propionamide | HO₂C–CH₂CH₂–S–(4-tolyl) | 473.4 | free base |
| 67 | N-(6-Methoxy-2-methyl-1-oxo-4-phenyl-1,2-dihydro-isoquinolin-3-ylmethyl)-3-o-tolylsulfanyl-propionamide | HO₂C–CH₂CH₂–S–(2-tolyl) | 473.4 | free base |
| 68 | N-(6-Methoxy-2-methyl-1-oxo-4-phenyl-1,2-dihydro-isoquinolin-3-ylmethyl)-3-(naphthalen-1-ylsulfany)-propionamide | HO₂C–CH₂CH₂–S–(1-naphthyl) | 509.5 | free base |

TABLE 2-continued

Reaction of 41 With Carboxylic Acids to Give Compounds 42–97

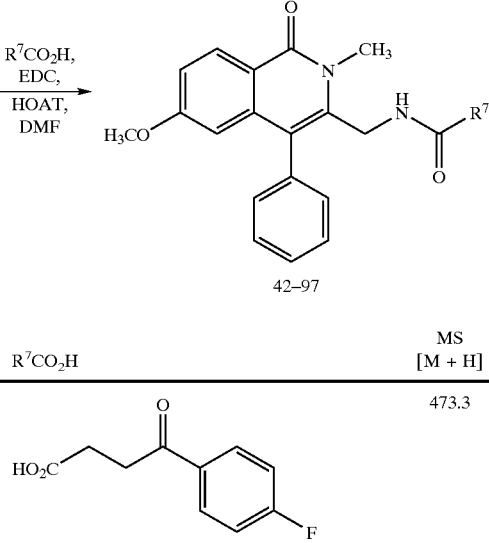

| No. | Compound Name | R⁷CO₂H | MS [M + H] | Salt Form |
|---|---|---|---|---|
| 69 | 4-(4-Fluoro-phenyl)-N-(6-methoxy-2-methyl-1-oxo-4-phenyl-1,2-dihydro-isoquinolin-3-ylmethyl)-4-oxo-butyramide | 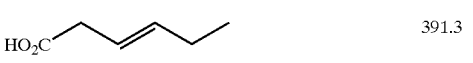 | 473.3 | free base |
| 70 | Hex-3-enoic acid (6-methoxy-2-methyl-1-oxo-4-phenyl-1,2-dihydro-isoquinolin-3-ylmethyl)-amide |  | 391.3 | free base |
| 71 | Acetic acid 1-[(6-methoxy-2-methyl-1-oxo-4-phenyl-1,2-dihydro-isoquinolin3-ylmethyl)-carbamoyl]-1-(R)-phenyl-methyl ester |  | 471.3 | free base |
| 72 | 2-(R)-Methoxy-N-(6-methoxy-2-methyl-1-oxo-4-phenyl-1,2-dihydro-isoquinolin-3-ylmethyl)-2-phenyl-acetamide | 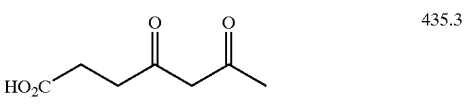 | 443.3 | free base |
| 73 | 4,6-Dioxo-heptanoic acid (6-methoxy-2-methyl-1-oxo-4-phenyl-1,2-dihydro-isoquinolin-3-ylmethyl)-amide | 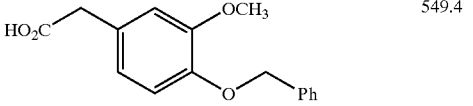 | 435.3 | free base |
| 74 | 2-(4-Benzyloxy-3-methoxy-phenyl)-N-(6-methoxy-2-methyl-1-oxo-4-phenyl-1,2-dihydro-isoquinolin-3-yl)-acetamide | 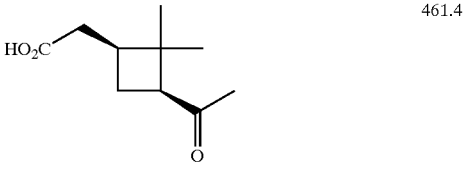 | 549.4 | free base |
| 75 | cis-2-(3-Acetyl-2,2-dimethyl-cyclobutyl)-N-(6-methoxy-2-methyl-1-oxo-4-phenyl-1,2-dihydro-isoquinolin-3-yl)-acetamide |  | 461.4 | free base |
| 76 | 3-Hydroxy-N-(6-methoxy-2-methyl-1-oxo-4-phenyl-1,2-dihydro-isoquinolin-3-ylmethyl)-2-phenyl-propionamide |  | 443.3 | free base |
| 77 | 1-Phenyl-cyclopropanecarboxylic acid (6-methoxy-2-methyl-1-oxo-4-phenyl-1,2-dihydro-isoquinolin-3-yl)-amide | | 439.3 | free base |

TABLE 2-continued

Reaction of 41 With Carboxylic Acids to Give Compounds 42–97

| No. | Compound Name | R⁷CO₂H | MS [M + H] | Salt Form |
|-----|---------------|--------|------------|-----------|
| 78 | N-(6-Methoxy-2-methyl-1-oxo-4-phenyl-1,2-dihydro-isoquinolin-3-ylmethyl)-3-(2-methoxy-phenyl)-propanamide | | 457.4 | free base |
| 79 | N-(6-Methoxy-2-methyl-1-oxo-4-phenyl-1,2-dihydro-isoquinolin-3-ylmethyl)-2-(6-methoxy-3-oxo-ndan-1-yl)-acetamide | | 497.4 | free base |
| 80 | 2-Cyclopentyl-N-(6-methoxy-2-methyl-1-oxo-4-phenyl-1,2-dihydro-isoquinolin-3-ylmethyl)-acetamide | | 403.3 | free base |
| 81 | 2-(2-Chloro-6-fluoro-phenyl)-N-(6-methoxy-2-methyl-1-oxo-4-phenyl-1,2-dihydro-isoquinolin-3-ylmethyl)-acetamide | | 465.3 | free base |
| 82 | 3-Cyclopentyl-N-(6-methoxy-2-methyl-1-oxo-4-phenyl-1,2-dihydro-isoquinolin-3-ylmethyl)-propionamide | | 419.4 | free base |
| 83 | 2-(6-Chloro-9H-carbazol-2-yl)-N-(6-methoxy-2-methyl-1-oxo-4-phenyl-1,2-dihydro-isoquinolin-3-ylmethyl)-2-methyl-acetamide | | 550.3 | free base |
| 84 | 2-(5-Fluoro-1H-indol-3-yl)-N-(6-methoxy-2-methyl-1-oxo-4-phenyl-1,2-dihydro-isoquinolin-3-ylmethyl)-acetamide | | 470.3 | free base |
| 85 | 1H-Indole-6-carboxylic acid (6-methoxy-2-methyl-1-oxo-4-phenyl-1,2-dihydro-isoquinolin-3-ylmethyl)-amide | | 438.3 | free base |
| 86 | N-(6-Methoxy-2-methyl-1-oxo-4-phenyl-1,2-dihydro-isoquinolin-3-ylmethyl)-3-phenylsulfanyl-propionamide | | 459.3 | free base |

TABLE 2-continued

Reaction of 41 With Carboxylic Acids to Give Compounds 42–97

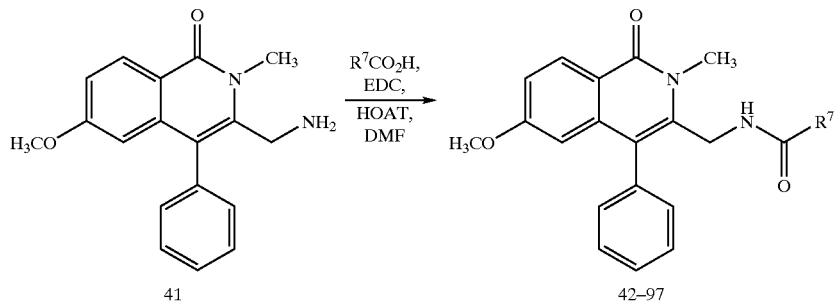

| No. | Compound Name | $R^7CO_2H$ | MS [M + H] | Salt Form |
|---|---|---|---|---|
| 87 | N-(6-Methoxy-2-methyl-1-oxo-4-phenyl-1,2-dihydro-isoquinolin-3-ylmethyl)-3-quinoxalin-2-ylsulfanyl)-propionamide | | 511.4 | free base |
| 88 | 3-(2,4-Dichloro-phenoxy)-N-(6-methoxy-2-methyl-1-oxo-4-phenyl-1,2-dihydro-isoquinolin-3-ylmethyl)-propionamide | | 511.4 | free base |
| 89 | N-(6-Methoxy-2-methyl-1-oxo-4-phenyl-1,2-dihydro-isoquinolin-3-ylmethyl)-3-phenoxy-benzamide | | 491.4 | free base |
| 90 | 2-(3-Fluoro-phenyl)-N-(6-methoxy-2-methyl-1-oxo-4-phenyl-1,2-dihydro-isoquinolin-3-ylmethyl)-acetamide | | 431.3 | free base |
| 91 | 4'-Trifluoromethyl-biphenyl-2-carboxylic acid (6-methoxy-2-methyl-1-oxo-4-phenyl-1,2-dihydro-isoquinolin-3-ylmethyl)-amide | | 543.4 | free base |
| 92 | N-(6-Methoxy-2-methyl-1-oxo-4-phenyl-1,2-dihydro-isoquinolin-3-ylmethyl)-4-phenoxy-benzamide | | 491.4 | free base |
| 93 | N-(6-Methoxy-2-methyl-1-oxo-4-phenyl-1,2-dihydro-isoquinolin-3-ylmethyl)-2-(4-methoxy-phenyl)-2-phenoxy-acetamide | | 535.4 | free base |
| 94 | 2-Benzyl-N-(6-methoxy-2-methyl-1-oxo-4-phenyl-1,2-dihydro-isoquinolin-3-ylmethyl)-benzamide | | 489.4 | free base |

TABLE 2-continued

Reaction of 41 With Carboxylic Acids to Give Compounds 42–97

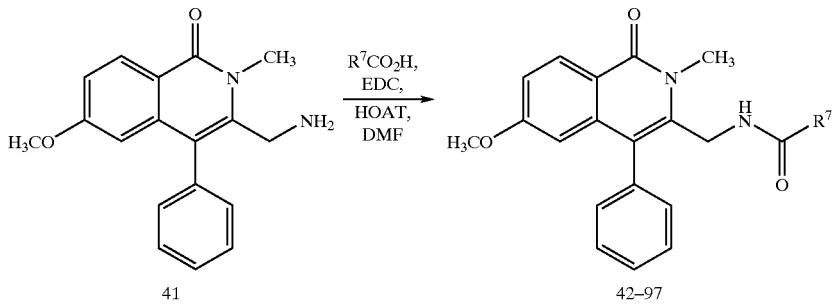

| No. | Compound Name | R⁷CO₂H | MS [M + H] | Salt Form |
|---|---|---|---|---|
| 95 | Biphenyl-2-carboxylic acid (6-methoxy-2-methyl-1-oxo-4-phenyl-1,2-dihydro-isoquinolin-3-ylmethyl)-amide | | 475.4 | free base |
| 96 | Biphenyl-3-carboxylic acid (6-methoxy-2-methyl-1-oxo-4-phenyl-1,2-dihydro-isoquinolin-3-ylmethyl)-amide | | 475.3 | free base |
| 97 | 2-(5-Methoxy-2-methyl-1H-indol-3-yl)-N-(6-methoxy-2-methyl-1-oxo-4-phenyl-1,2-dihydro-isoquinolin-3-ylmethyl)-acetamide | | 496.4 | free base |

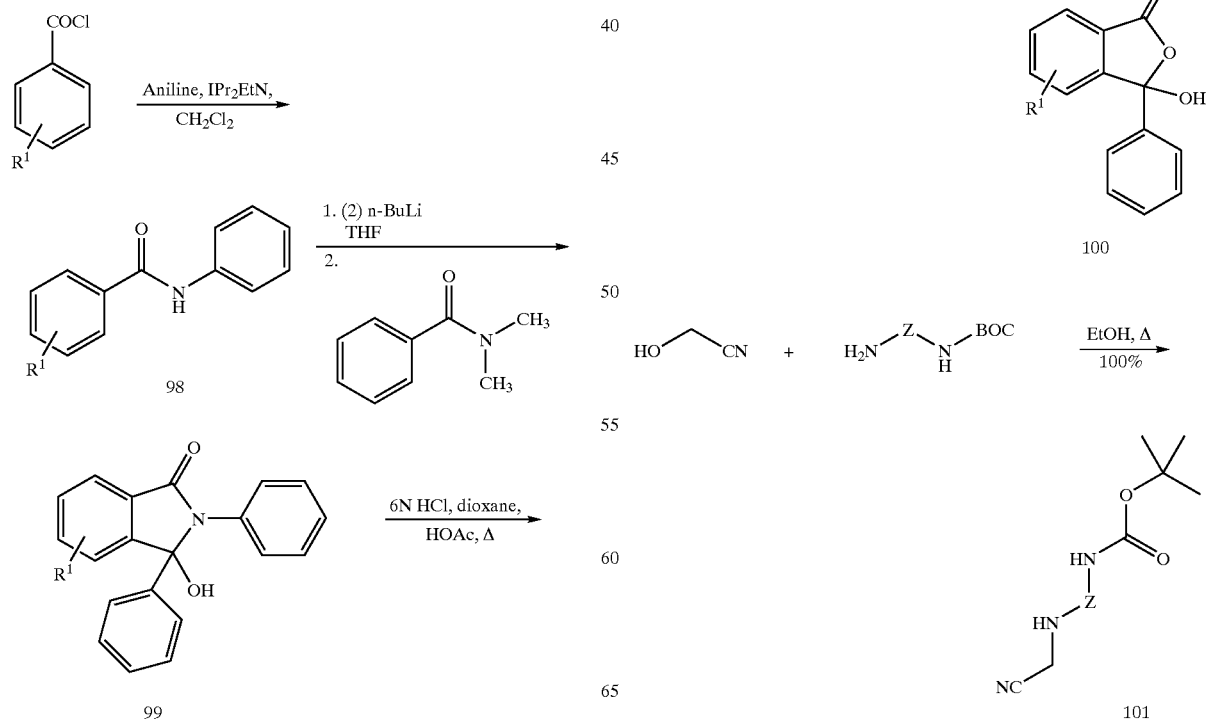

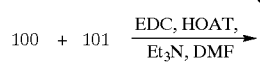

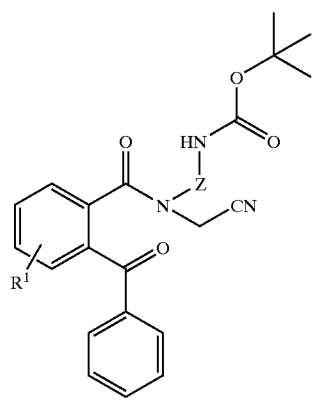 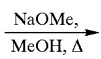

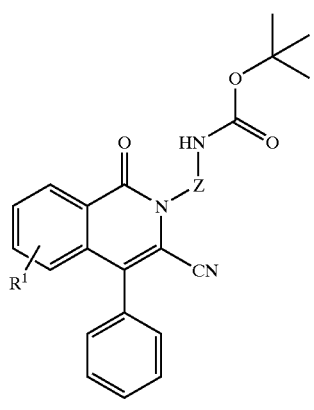 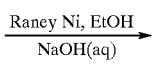

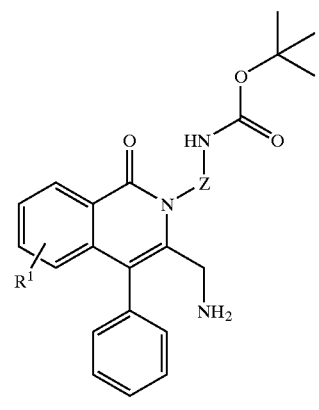 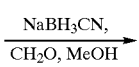

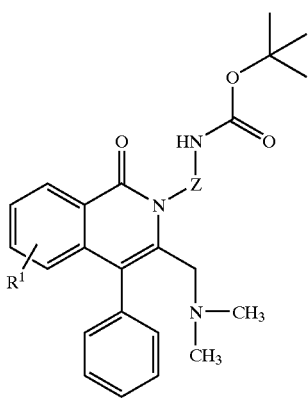

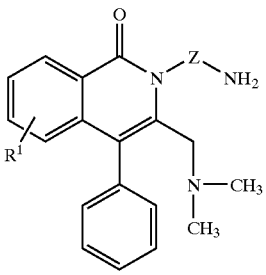

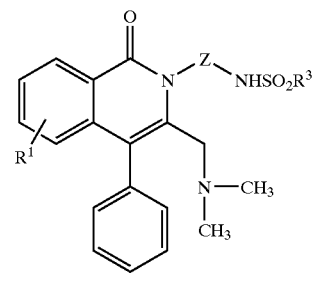

In Reaction Scheme C, compound 99 was prepared in the same way as described in Reaction Scheme A. The compound 100 was produced by a hydrolysis followed by hemiketal formation. The compound 100 then reacted with compound 101 to form amide compound of 102, which is then cyclized in the presence of base to form compound 103. The nitrile reduction of compound 103 gave compound 104, which undergoes reductive alkylation to give compound 105. The removal of protecting group (BOC) in compound 105 afforded 106, which is then reacted with sulfonyl chloride to give the final product of sulfonamide compound 107. Table 3 below provides the compounds that were prepared in accordance with Reaction Scheme C.

TABLE 3

Reaction of 116 With Sulfonyl Chlorides to Give Sulfonamide Compounds 118–132

| No. | Name | R³SO₂Cl | MS [M + H]⁺ | Salt Form |
|-----|------|---------|-------------|-----------|
| 117 | N-[2-(3-Dimethylaminomethyl-6-methoxy-1-oxo-4-phenyl-1H-isoquinolin-2-yl)-ethyl] methanesulfonamide | CH₃SO₂Cl | 430.3 | free base |
| 118 | N-[2-(3-Dimethylaminomethyl-6-methoxy-1-oxo-4-phenyl-1H-isoquinolin-2-yl)-ethyl]-2-trifluoromethoxy-benzenesulfonamide | 2-(OCF₃)-C₆H₄-SO₂Cl | 576.3 | free base |
| 119 | Butane-1-sulfonic acid [2-(3-dimethylaminomethyl-6-methoxy-1-oxo-4-phenyl-1H-isoquinolin-2-yl)-ethyl]-amide | n-BuSO₂Cl | 472 | free base |
| 120 | Propane-2-sulfonic acid [2-(3-dimethylaminomethyl-6-methoxy-1-oxo-4-phenyl-1H-isoquinolin-2-yl-ethyl]-amide | iPrSO₂Cl | 458 | free base |
| 121 | Naphthalene-2-sulfonic acid [2-(3-dimethylaminomethyl-6-methoxy-1-oxo-4-phenyl-1H-isoquinolin-2-yl)-ethyl]-amide | 2-NaphSO₂Cl | 542.6 | free base |
| 122 | Thiophene-2-sulfonic acid [2-(3-dimethylaminomethyl-6-methoxy-1-oxo-4-phenyl-1H-isoquinolin-2-yl)-ethyl]-amide | 2-ThienylSO₂Cl | 498.3 | free base |
| 123 | N-[2-(3-Dimethylaminomethyl-6-methoxy-1-oxo-4-phenyl-1H-isoquinolin-2-yl)-ethyl] benzenesulfonamide | PhSO₂Cl | 492.3 | free base |
| 124 | N-[2-(3-Dimethylaminomethyl-6-methoxy-1-oxo-4-phenyl-1H-isoquinolin-2-yl)-ethyl]-4-methoxy-benzenesulfonamide | 4-(OCH₃)-C₆H₄-SO₂Cl | 522.3 | free base |
| 125 | N-[2-(3-Dimethylaminomethyl-6-methoxy-1-oxo-4-phenyl-1H-isoquinolin-2-yl)-ethyl]-4-methyl-benzenesulfonamide | 4-(CH₃)-C₆H₄-SO₂Cl | 506.3 | free base |
| 126 | N-[2-(3-Dimethylaminomethyl-6-methoxy-1-oxo-4-phenyl-1H-isoquinolin-2-yl)-ethyl]-bis-3,5-(trifluoromethyl)-benzenesulfonamide | 3,5-(CF₃)₂-C₆H₃-SO₂Cl | 628 | free base |

TABLE 3-continued

Reaction of 116 With Sulfonyl Chlorides to Give Sulfonamide Compounds 118–132

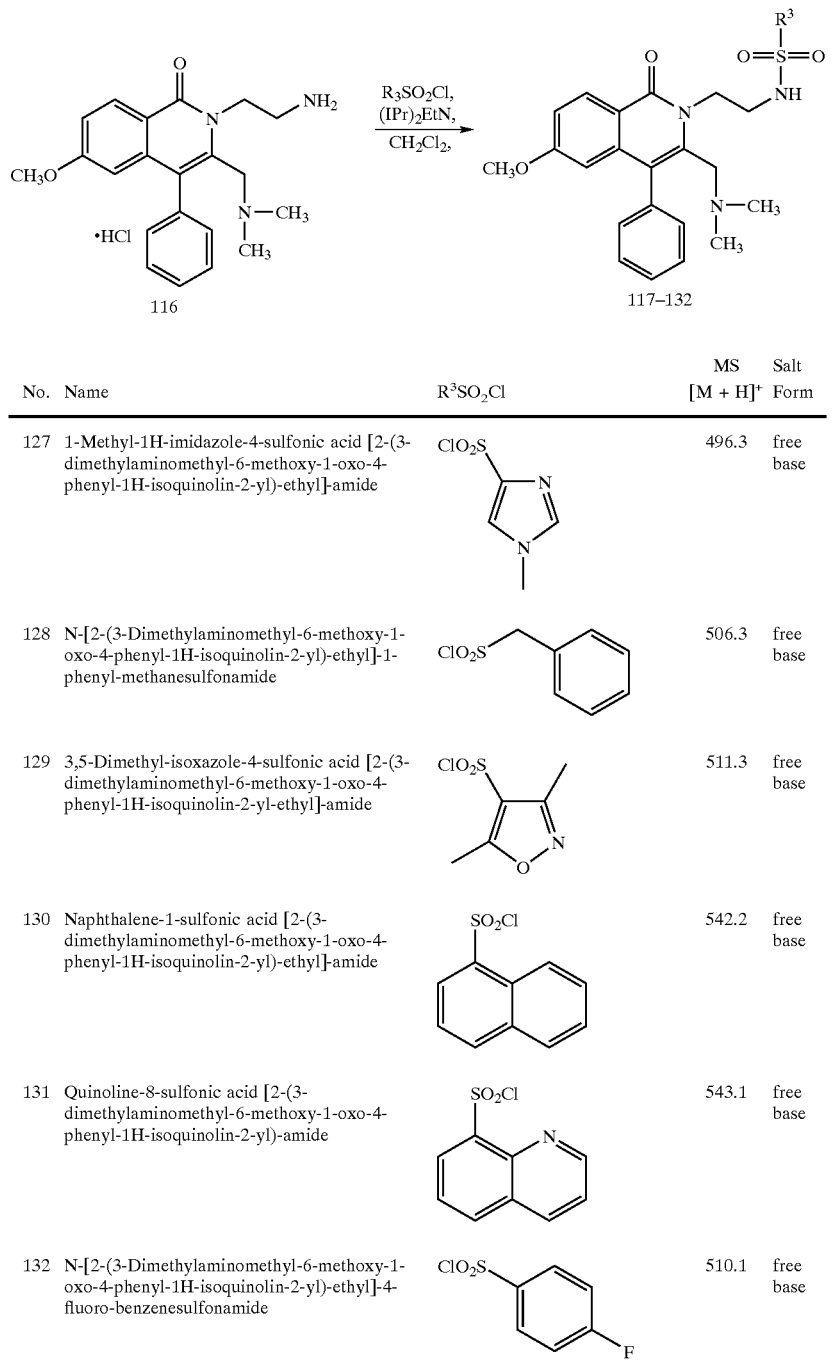

| No. | Name | R³SO₂Cl | MS [M + H]⁺ | Salt Form |
|---|---|---|---|---|
| 127 | 1-Methyl-1H-imidazole-4-sulfonic acid [2-(3-dimethylaminomethyl-6-methoxy-1-oxo-4-phenyl-1H-isoquinolin-2-yl)-ethyl]-amide | | 496.3 | free base |
| 128 | N-[2-(3-Dimethylaminomethyl-6-methoxy-1-oxo-4-phenyl-1H-isoquinolin-2-yl)-ethyl]-1-phenyl-methanesulfonamide | | 506.3 | free base |
| 129 | 3,5-Dimethyl-isoxazole-4-sulfonic acid [2-(3-dimethylaminomethyl-6-methoxy-1-oxo-4-phenyl-1H-isoquinolin-2-yl-ethyl]-amide | | 511.3 | free base |
| 130 | Naphthalene-1-sulfonic acid [2-(3-dimethylaminomethyl-6-methoxy-1-oxo-4-phenyl-1H-isoquinolin-2-yl)-ethyl]-amide | | 542.2 | free base |
| 131 | Quinoline-8-sulfonic acid [2-(3-dimethylaminomethyl-6-methoxy-1-oxo-4-phenyl-1H-isoquinolin-2-yl)-amide | | 543.1 | free base |
| 132 | N-[2-(3-Dimethylaminomethyl-6-methoxy-1-oxo-4-phenyl-1H-isoquinolin-2-yl)-ethyl]-4-fluoro-benzenesulfonamide | | 510.1 | free base |

The specificity and utility of the exemplified compound as antiarrhythmic agent is shown by the following voltage-clamp studies in CHO cells expressing human $K_v1.5$ and in isolated human atrial myocytes and guinea pig isolated ventricular myocytes in vitro. Assays for assessing the activity of particular compounds may employ cells stably transfected to express a specific potassium channel as well as native mammalian cells. For example, cells stably transfected to express a specific potassium channel, which have been treated with a voltage dependent fluorescent dye, can be used to gauge the inhibitory activity of potassium channel inhibitor compounds, possibly in comparison to known inhibitors. Alternatively, such cells can be primed with a detectable species, such as $^{86}$Rb, and the challenged with a particular compound, under conditions otherwise suitable for activating potassium channel, to assess the potassium inhibitory activity of the compound. The potassium channel inhibitory activity of a compound also can be determined using isolated mammalian cells and the whole cell configuration of the known patch clamp technique (Hamill et al., *Pflugers Archiv* 391:85, 1981). These and other known techniques can be readily employed by those skilled in the art to assess the activity level of the potassium channel inhibitor compounds contemplated by the present invention.

Voltage Clamp Measurement of Ionic Currents in Vitro

A. Measurement of $K_v1.5$ in CHO Cells

Expression of $K_v1.5$ in CHO Cells

A cDNA encoding $K_v1.5$, isolated from a human fetal heart library, was subcloned into pcDNAI/Neo (Invitrogen) as a Hind III—Xba I fragment.

CHOKI cells were plated at $2.7 \times 10^4$ cells/60 mm dish and incubated at 37° C. in a 5% $CO_2$ environment for three days. Cells were then washed twice and covered with 3 ml of OptiMEM medium (Gibco). Plasmid/DOTAP solution (consisting of 5 mg of $K_v1.5$ in pcDNAI/Neo and 30 mg DOTAP transfection reagent (Boehringer Mannheim) in 1 ml of OptiMEM) was added dropwise to each plate while swirling. Plates were incubated overnight and the media then changed to 5 mls of F12 (Gibco) supplemented with 10% FBS (Sigma), 1,000 U/ml penicillin 1,000 mg/ml streptomycin (Gibco), and 2 mM glutamine (Gibco). After two more days, the cells were trypsinized and replated on 100 mm dishes in supplemented F12 media including 1 mg/ml G418 (Gibco). The medium was changed daily until nontransfected cells were killed. Cell lines were grown from individual clones and tested for expression of $K_v1.5$ using both the $^{86}RB$ efflux assay and voltage clamp protocols. Lines exhibiting the highest level of expression were then recloned by serial dilution. These cells were maintained in culture and on each experimental day were freshly isolated by mild trypsinization.

Voltage Clamp Technique

CHO cells plated on glass coverslips were placed in a 1-ml chamber mounted on the stage of an inverted microscope, and perfused at 2–3 ml/min with the following solution (in mM/L): 132 NaCl, 4 KCl, 1.2 $MgCl_2$, 10 HEPES (formal name: N-2-hydroxyethyl piperazine-N'-2-ethanesulfonic acid), 11.1 glucose. $CaCl_2$ (0.5–1.8 mM) was present in some experiments, and had no effects on $K_v1.5$. Nisoldipine (0.4 mM–1.0 mM), a relatively specific blocker of L-type $Ca^{2+}$ channels was present in all experiments. The patch-clamp technique was used to record ionic currents in the whole-cell configuration. Patch pipettes were obtained using a two stage puller from square bore (1.0 mm o.d.) borosillicate capillary tubing. Pipettes were filled with the following solution (in mM/L): 110 K-Gluconate or K-Aspartate, 20 KCl, 5 MgATP, 5 EGTA, 5–10 HEPES, pH 7.2. The electrodes had tip resistances ranging from 3 to 10 Mohm when filled with this solution. Following seal formation, the membrane was ruptured by gentle suction to establish the whole-cell configuration, and negative pressure was maintained on the pipette using a 1 ml gas-tight syringe attached via air tight tubing to the suction port of the microelectrode holder. Series resistance was compensated 70–85%. Currents were sampled at 5 kHz using an Axopatch 200 A amplifier (Axon Instruments) or a List EPC-7 clamp amplifier (List Electronic) and were low pass filtered at 1 kHz. Data acquisition and analysis were performed using pClamp soft ware (Axon Instruments) and an IBM compatible 486 computer.

Measurements of $K_v1.5$ Expressed Currents $K_v1.5$ currents were elicited by 150 ms depolarizing test pulses to +40 mV from a holding potential of −80 mV. The effects of test agents were assessed at steady state. Data was analyzed as % block from control current amplitude. The amplitude of $K_v1.5$ was measured as the amplitude of the time-dependent net outward current at the end of the test pulse, relative to the holding current level. $IC_{50}$ for rested state and use-dependent block were determined from the first and tenth pulses, respectively, during a series of 10 consecutive pulses delivered at 1 Hz. All experiments were performed at room temperature (22–24° C.).

B. Measurement of $I_{Kur}$ in Human Atrial Myocytes

Isolation of Human Atrial Myocytes

Human myocytes were isolated from specimens of right atrial appendage obtained from patients undergoing cardiopulmonary bypass, using a modification of the procedure described by Fermini, B., Wang, Z., Duan, D. and Nattel, S., "Differences in rate dependence of transient outward current in rabbit and human atrium" *Am. J. Physiol.* 263:H1747–H1754 (1992). All tissues were collected in accordance with Temple University School of Medicine Institutional guidelines. All atrial specimens were grossly normal at the time of excision. Tissue samples were quickly immersed in cold (0–4° C.) cardioplegia solution containing (in mM/L): 50 $KH_2PO_2$, 8$MgSO_4$, 10$NaHCO_3$, 5 adenosine, 25 taurine, 140 glucose, and 100 mannitol, pH 7.4 and bubbled with 100% $O_2$. Specimens were minced into 0.5–1 mm cubes and transferred to a 50-ml conical tube containing an ultra low calcium wash solution containing (in mM/L): 137 NaCl, 5 $KH_2 PO_4$, 1 $MgSO_4$, 10 taurine, 10 glucose, 5 HEPES and 0.1 EGTA (formal name: Ethyleneglycol-bis-(b-aminoethyl ether) N,N,N',N'-tetraacetic acid), pH 7.4 (22–24° C.). The tissue was gently agitated by continuous bubbling with 100% $O_2$ for 5 min. The tissue was then incubated in 5 ml of solution containing (in mM/L): 137 NaCl, 5 $KH_2 PO_4$, 1$MgSO_4$, 10 taurine, 10 glucose, and 5 HEPES supplemented with 0.1% bovine albumin, 1.5 mg/ml collagenase CLS II (Worthington Biochemical), and 1.0 mg/ml protease type XXIV (Sigma Chemical Co.), pH 7.4 (37° C.), and bubbled continuously with 100% $O_2$. The supernatant was removed after 40 min and discarded. The chunks were then incubated in a solution of the same ionic composition but supplemented with only collagenase and 100 mM $CaCl_2$. Microscopic examination of the medium was performed every 10–20 min to determine the number and quality of isolated cells. When the yield appeared maximal, the tissue chunks were suspended in a modified Kraftbruhe solution containing (in mM/L): 25 KCl, 10 $KH_2PO_4$, 25 taurine, 0.5 EGTA, 22 glucose, 55 glutamic acid, and 0.1% bovine albumin, pH 7.3 (22–24° C.) and gently triturated using a large bore Pasteur pipette. The supernatant was collected in a 50 ml centrifuge tube. The cell suspension was centrifuged for 2 min at 1000 rpm and the resulting pellet was resuspended in 0.2 mM HBS solution containing (in mM/L): 132 NaCl, 4 KCl, 1.2 $MgCl_2$, 10 HEPES and 11.1 glucose, pH 7.2. Cells were used within 2–24 hr after isolation.

Voltage-clamp Technique

A small aliquot of the solution containing the isolated human atrial myocytes was placed in a 1-ml chamber mounted on the stage of an inverted microscope. Five minutes were allowed for cell adhesion to the bottom of the chamber. To record $I_{Kur}$, human atrial myocytes were superfused with a solution of the same ionic composition as that used for $K_v1.5$. An alternative external solution was sometimes used in which NaCl was replaced with NMDG (formal name: N-methyl-d-glucamine) to inhibit $I_{Na}$. NMDG had no effects on $I_{Kur}$ and there were no notable quantitative differences in the degree of block of $I_{Kur}$ with these two conditions.

Currents were elicited by 150 ms depolarizing test pulses to +40 mV from a holding potential of −50 mV to inactivate $I_{to}$ and $I_{Na}$. The amplitude of $I_{Kur}$ was measured as the amplitude of the time-dependent current at the end of the test pulse, relative to the holding current level. Similar to $K_v1.5$, the effects of all drugs were studied only when steady-state changes were achieved and data was analyzed as % block from control currents. $IC_{50}$ for rested state and use-dependent block was determined from the first and tenth pulses, respectively, during a series of 10 consecutive pulses delivered at 1 Hz. All experiments were performed at room temperature (22–24° C.).

C. Measurement of Use-Dependent and Rate-Dependent Block

Use-dependent and rate-dependent block were assessed by measuring the currents elicited during trains of 150 msec long depolarizing pulses to a test potential of +40 mV from holding potentials of −80 mV and −50 mV in CHO cells and human atrial myocytes, respectively. Pulses were applied in 10 second long trains delivered after 30 second rest intervals at frequencies of 1 Hz (10 pulses) or 3 Hz (30 pulses). Percent block of the current is defined as the % decrease in the current amplitude produced by an agent during a given pulse relative to the control current amplitude for that pulse. Rested-state block is the block of the current during the first pulse in a train following the 30 second rest period. Use dependent block is block that occurs to a progressively greater extent with each successive depolarization in a train or sequence of pulses or depolarizations delivered at a given rate or frequency. Thus, during a train of 10 depolarizations at frequency of 1 Hz, use-dependent block is assessed as the ratio of the amount of block for the 10th pulse relative to block for the 1st pulse (rested state block) of the train. Rate-dependent block is block that occurs to a greater extent or preferentially at faster rates of depolarization or heart rates. Thus, rate-dependent block is assessed as the ratio of the amount of block of the current during the last pulse of the 10 second train at 3 Hz vs. 1 Hz. Consequently, ratios of less than one (<1) are indicative of use-dependent and rate-dependent block and the lower the ratio the greater the degree of use and rate dependence.

While the invention has been described and illustrated with reference to certain particular embodiments thereof, those skilled in the art will appreciate that various adaptations, changes, modifications, substitutions, deletions, or additions of procedures and protocols may be made without departing from the spirit and the scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected for whether there are present pharmaceutical carriers, as well as the type of formulation and mode of administration employed, and such expected variations or differences in the results are contemplated in accordance with the objects and practices of the present invention. It is intended therefore, that the invention be defined by the scope of the claims and that such claims be interpreted as broadly as is reasonable.

The following examples illustrate the preparation of the compounds of Formula I and as such are not to be considered as limiting the invention set forth in the claims appended hereto.

EXAMPLE 1

Reaction scheme of 3-Dimethylaminomethyl-6-methoxy-2-methyl-4-phenyl-2H-isoquinolin-1-one Hydrochloride(14)

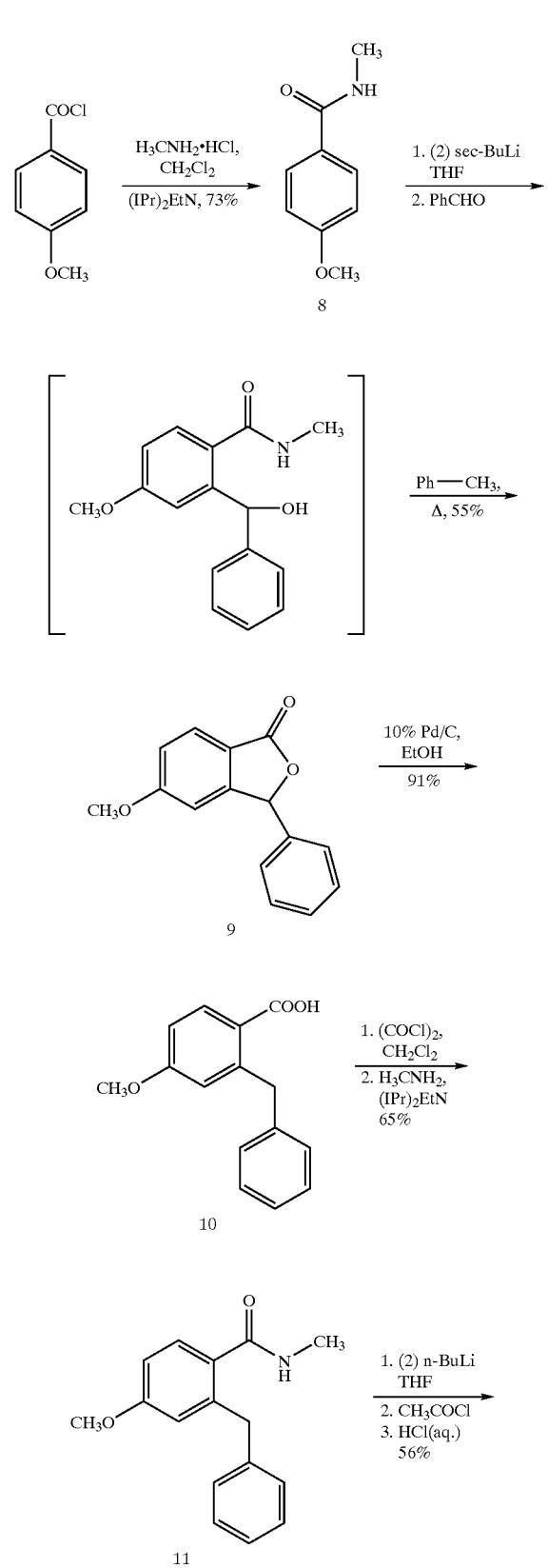

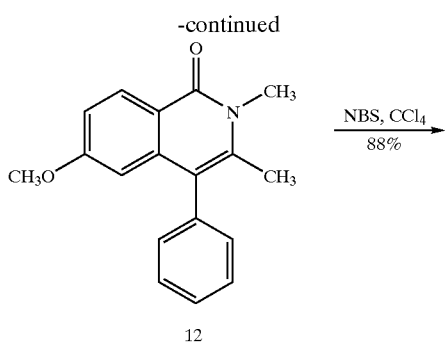

12

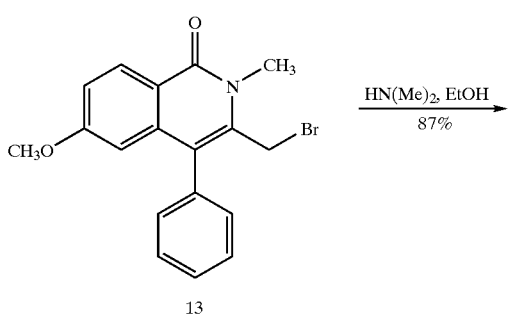

13

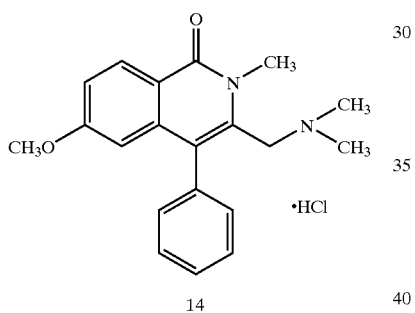

14

EXAMPLE 2

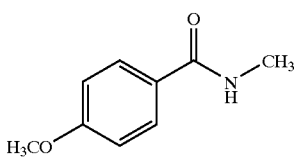

4-Methoxy-N-methyl-benzamide (8)

An addition funnel containing p-anisoyl chloride (47.6 g, 279 mmol) and methylene chloride (125 mL) was attached to a 2 L 3-neck round bottom flask containing 375 mL methylene chloride. The reaction flask was cooled in an ice bath and methylamine (g) was bubbled through the solvent. The contents of the addition funnel were added dropwise. A white precipitate appeared. Warmed to room temperature and stirred for 24 h. Washed with water; separated layers and dried the organic portion with sodium sulfate (anh.). Removal of the solvent in vacuo followed by trituration with hexane/ether gave 8 as a white solid (33.7 g, 204 mmol, 73.2%)

$^1$HNMR (CHCl$_3$, 300 MHz) δ 7.80 (d, 2H); 6.95 (d, 2H); 6.10 (s, br, 1H); 3.85 (s, 3H), 3.00 (d, 3H).

EXAMPLE 3

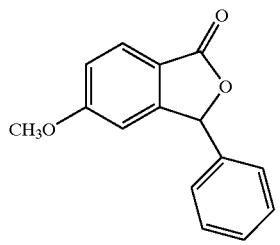

5-Methoxy-3-phenyl-3H-isobenzofuran-1-one (9)

A solution of 8 (15 g, 91 mmol) in THF was cooled to −70° C. under Argon. To this was added sec-butyllithium (147 mL, 1.3M). After stirring 0.5 h a tan suspension resulted. Added benzaldehyde (9.2 mL, 91 mmol.) and stirred 1 h. Quenched with ice then removed THF in vacuo. Added sat. sodium bicarbonate and extracted with ethyl acetate (4x). Dried the combined organic portions with sodium sulfate (anh.) and removed the solvent in vacuo. Added toluene and heated to reflux for 18 h. Removal of the solvent in vacuo followed by trituration with hexane/ether gave unreacted starting material 8 (4.63 g). Concentration of the filtrate in vacuo followed by flash column chromatography (hexane:ethyl acetate 80:20) gave 9 as a yellow solid (12.0 g, 50.1 mmol, 55.1%)

$^1$HNMR (CHCl$_3$, 300 MHz) δ 7.90 (d, 1H); 7.40–7.20 (m, 4H); 7.05 (d, 1H); 6.75 (s, 1H), 6.30 (s, 1H); 3.82 (s, 3H).

EXAMPLE 4

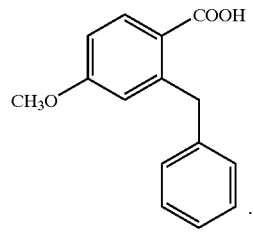

2-Benzyl-4-methoxy-benzoic acid (10)

To a solution of 9 (12.0 g, 50 mmol) in ethanol was added 10% palladium on carbon (1.5 g). The resulting suspension was hydrogenated at 60 psi for 18 h. Filtration through celite followed by removal of the solvent in vacuo gave 10 as a white solid (11.0 g, 45.5 mmol, 91.1%).

$^1$HNMR (CHCl$_3$, 300 MHz) δ 8.10 (d, 1H); 7.40–7.20 (m, 5H); 6.81 (d, 1H); 6.70 (s, 1H), 4.42 (s, 2H); 3.90 (s, 3H).

EXAMPLE 5

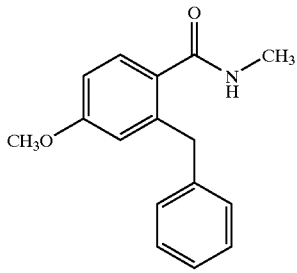

2-Benzyl-4-methoxy-N-methyl-benzamide (11)

To an ice bath cooled solution of 10 (11.8 g, 48.8 mmol) in methylene chloride under Argon was added oxalyl chloride (5.10 mL, 58.5 mmol). Added a few drops of DMF and warmed to room temperature. After 18 h the solvent was removed in vacuo. Methylene chloride and methylamine hydrochloride (6.54 g, 97.6 mmol) were added and the contents of the reaction flask were cooled in an ice bath. Diisopropylethylamine was added dropwise using an addition funnel. After 3 h the reaction solution was washed with 5% potassium bisulfate, sat. sodium bicarbonate, and brine. Dried the organic layer with sodium sulfate (anh.) and removed the solvent in vacuo. Trituration with hexane/ether gave 11 as a light solid (8.15 g, 32.0 mmol, 65.5%).

$^1$HNMR (CHCl$_3$, 300 MHz) δ 7.40–7.10 (m, 6H); 6.78 (m, 2H); 5.50 (s, br, 1H); 4.20 (s, 2H), 3.80 (s, 3H); 2.82 (d, 3H).

EXAMPLE 6

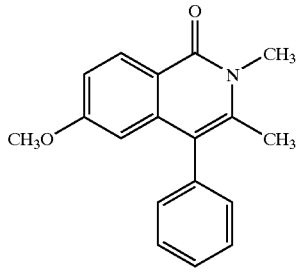

6-Methoxy-2,3-dimethyl-4-phenyl-2H-isoquinolin-1-one (12)

To a solution of 11 (5.00 g, 19.6 mmol) in THF under Argon at −70° C. was added n-butyllithium (18.8 mL, 2.5M). After 0.5 h acetyl chloride (2.10 mL, 29.4 mmol) was added. Stirred 0.5 h then added water and warmed to room temperature. Removed the solvent in vacuo and added 1N hydrochloric acid. Extracted with ethyl acetate (4×) and dried the combined organic portions with magnesium sulfate (anh.). Removal of the solvent in vacuo followed by trituration with ether gave 12 as a light solid (2.54 g, 9.10 mmol, 46.4%).

$^1$HNMR (CHCl$_3$, 300 MHz) δ 8.40 (d, 1H); 7.55–7.40 (m, 3H); 7.23 (m, 2H); 7.00 (m, 2H); 6.28 (m, 1H); 3.85 (s, 6H); 2.20 (s, 3H).

EXAMPLE 7

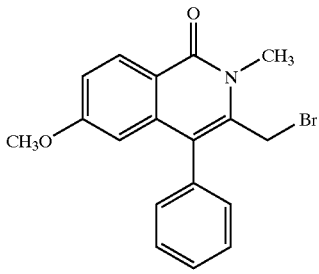

3-Bromomethyl-6-methoxy-2-methyl-4-phenyl-2H-isoquinolin-1-one (13)

To a solution of 12 (3.08 g, 11.0 mmol) in carbon tetrachloride under Argon was added N-bromosuccinimide (1.96 g, 11.0 mmol). The contents of the reaction flask were heated to reflux. After 3 h an additional portion of N-bromosuccinimide (0.50 g, 2.81 mmol) was added to the reaction flask. After 7 h the solvent was removed in vacuo and sat. sodium bicarbonate was added. Extracted with methylene chloride (4×) and dried the combined organic portions with magnesium sulfate (anh.). Removal of the solvent in vacuo followed by trituration with ether gave 13 as a light solid (3.47 g, 9.70 mmol, 88.2%)

$^1$HNMR (CHCl$_3$, 300 MHz) δ 8.41 (d, 1H); 7.60–7.50 (m, 3H); 7.40 (m, 2H); 7.05 (m, 2H), 6.28 (s, 1H); 4.28 (s, 2H); 3.80 (s, 3H); 3.65 (s, 3H).

EXAMPLE 8

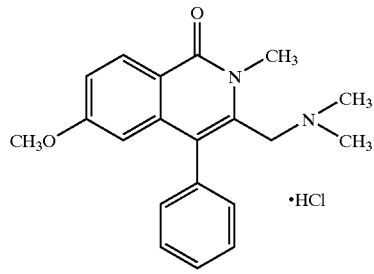

3-Dimethylaminomethyl-6-methoxy-2-methyl-4-phenyl-2H-isoquinolin-1-one Hydrochloride (14)

An ice bath cooled solution of 6 (3.47 g, 9.70 mmol) in ethanol was saturated with dimethylamine (g). The resulting solution was heated in a Parr pressure reactor at 60° C. for 5 h. The solvent was removed in vacuo and sat. sodium bicarbonate was added. Extracted with methylene chloride (4×) and dried the combined organic portions with magnesium sulfate (anh.). Removal of the solvent in vacuo followed by flash column chromatography (hexane:ethyl acetate 60:40) gave a white solid after removal of the solvent in vacuo. Dissolved in ethyl acetate and cooled in an ice bath. Addition of 1N hydrogen chloride in ether gave a white solid (14) which was isolated by vacuum filtration (3.00 G, 8.40 mmol, 86.6%).

$^1$HNMR (CHCl$_3$, 300 MHz) δ 12.60 (s, br, 1H); 8.45 (d, 1H); 7.60 (m, 3H); 7.25 (m, 2H), 7.15 (m, 1H); 6.38 (s, 1H); 4.30 (s, br, 2H); 4.00 (s, 3H); 3.70 (s,3H); 2.62 (s, 6H).

Compounds 16–38 were prepared using a procedure similar to that described for compound 14. These substances are summarized in Table 1.

EXAMPLE 9

3-(Isobutylamino-methyl)-2-methyl-4-phenyl-2H-isoquinolin-1-one (17)

$^1$HNMR (CDCl$_3$, 300 MHz) δ 8.52–8.46 (m, 1H); 7.52–7.40 (m, 5H); 7.29–7.23 (m, 2H); 6.99–6.96 (m, 1H); 3.87 (s, 3H); 3.45 (s, 2H); 2.26 (d, 2H); 1.58 (m, 1H); 0.82 (d,6H).

EXAMPLE 10

6-Methoxy-2-methyl-3-(4-methyl-piperidin-1-ylmethyl)-4-phenyl-2H-isoquinolin-1-one (24)

$^1$HNMR (CDCl$_3$, 300 MHz) δ 8.43 (d, 1H); 7.45 (M, 3H); 7.21–7.18 (m, 2H); 7.01 (m, 1H); 6.28 (d, 1H); 3.85 (s, 3H); 3.66 (s, 3H); 2.74 (m, 2H); 1.78–1.70 (m, 2H); 1.50 (m, 2H); 1.21–1.06 (m, 3H); 0.84 (d, 3H).

EXAMPLE 11

3-(2,3-Dihydro-indol-1-ylmethyl)-6-methoxy-2-methyl-4-phenyl-2H-isoquinolin-1-one (26)

$^1$HNMR (CDCl$_3$, 300 MHz) δ 8.46 (d, 1H); 7.48–7.36 (m, 3H); 7.24 (m, 2H); 7.08 (m, 3H); 6.69 (m, 1H); 6.52 (m, 1H); 6.36 (d, 1H); 4.09 (s, 2H); 3.78 (s, 3H); 3.69 (s, 3H); 3.08 (t, 2H); 2.84 (t, 2H).

EXAMPLE 12

6-Methoxy-2-methyl-4-phenyl-3-piperidin-1-ylmethyl-2H-isoquinolin-1-one (28)

$^1$HNMR (CDCl$_3$, 300 MHz) δ 8.43 (d, 1H); 7.44 (m, 3H); 7.20 (m, 2H); 7.02 (m, 1H); 6.29 (d, 1H); 3.86 (s, 3H); 3.66 (s, 3H); 3.29 (s, 2H); 2.28 (m, br, 4H); 1.46 (m, 4H); 1.32 (m, 2H).

EXAMPLE 13

3-[(tert-Butyl-methyl-amino)-methyl]-6-methoxy-2-methyl-4-phenyl-2H-isoquinolin-1-one (30)

$^1$HNMR (CDCl$_3$, 300 MHz) δ 8.41 (d, 1H); 7.46–7.35 (m, 3H); 7.21–7.28 (m,2H); 7.01 (dd, 1H); 6.30 (d, 1H); 3.93 (s, 3H); 3.66 (s, 3H); 3.52 (s,2H); 1.98 (s, 3H); 0.98 (s, 9H).

EXAMPLE 14

3-[(Ethyl-methyl-amino)-methyl]-6-methoxy-2-methyl-4-phenyl-2H-isoquinolin-1-one (32)

$^1$HNMR (CDCl$_3$, 300 MHz) δ 8.43 (d, 1H); 7.44 (m, 3H); 7.19 (m, 2H); 7.02 (m, 1H); 6.30 (d, 1H); 3.86 (s, 3H); 3.67 (s, 3H); 3.34 (s, 2H); 2.31 (q, 2H); 2.04 (s, 3H); 0.95 (t, 3H).

EXAMPLE 15

6-Methoxy-2-methyl-3-methylaminomethyl-4-phenyl-2H-isoquinolin-1-one (33)

$^1$HNMR (CDCl$_3$, 300 MHz) δ 8.42 (d, 1H); 7.46 (m, 3H); 7.25 (m, 2H); 7.01 (m, 1H); 6.32 (d, 1H); 3.82 (s, 3H); 3.67 (s, 3H); 3.45 (s, 2H); 2.92 (s, 3H).

EXAMPLE 16

3-[(Isopropyl-methyl-amino)-methyl]-6-methoxy-2-methyl-4-phenyl-2H-isoquinolin-1-one (34)

$^1$HNMR (CDCl$_3$, 300 MHz) δ 8.42 (d, 1H); 7.45–7.38 (m, 3H); 7.24–7.18 (m, 2H); 7.01 (dd, 1H); 6.32 (d, 1H); 3.84 (s, 3H); 3.67 (s, 3H); 3.41 (s, 2H); 2.80 (m, 1H); 1.98 (s, 3H); 0.80 (d, 6H).

EXAMPLE 17

EXAMPLE 18

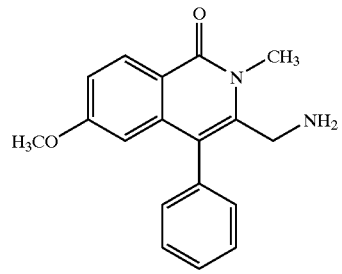

3-Aminomethyl-6-methoxy-2-methyl-4-phenyl-2H-isoquinolin-1-one (41)

A solution of 13 (1.50 g, 4.19 mmol) in ethanol was cooled to 0° C. in a threaded pressure tube. Ammonia gas was bubbled through the solution for 10 min. then the vessel was sealed and heated to 60° C. for 48 h. The contents of the pressure tube were cooled then the solvent was removed in vacuo and sat. sodium bicarbonate was added. Extracted with ethyl acetate (3×) and dried the combined organic portions, with sodium sulfate (anh.). Concentration of the filtrate in vacuo followed by flash column chromatography (methylene chloride:methanol:ammonium hydroxide 90:10:1) gave 41 as a white solid (864 mg, 2.94 mmol, 70.1%).

$^1$HNMR (CHCl$_3$, 300 MHz) δ 8.42 (d, 1H); 7.55–7.45 (m, 3H); 7.31–7.25 (m, 2H); 7.05 (dd, 1H), 6.32 (d, 1H); 3.83 (s, 1H); 3.67 (s, 3H); 3.65 (s, 2H); 1.22 (s, br, 2H).

Reaction scheme of 5-Phenyl-pentanoic acid (6-methoxy-2-methyl-1-oxo-4-phenyl-1,2-dihydro-isoquinolin-3-ylmethyl)-amide (42)

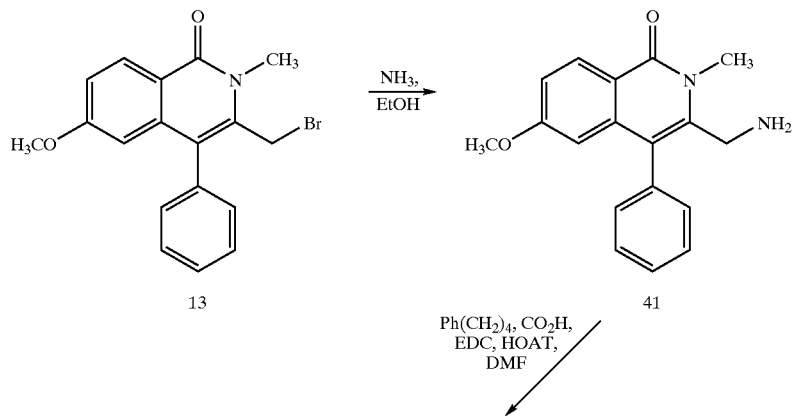

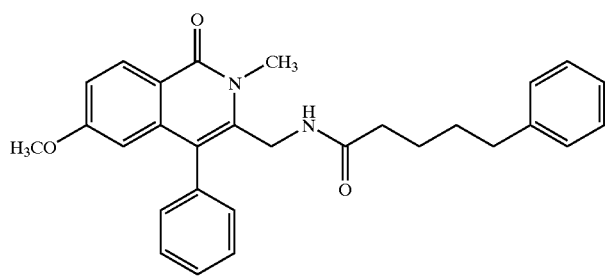

42

EXAMPLE 19

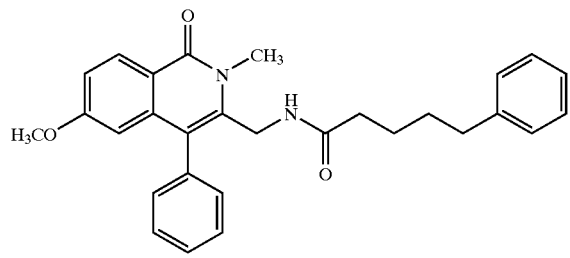

5-Phenyl-pentanoic acid (6-methoxy-2-methyl-1-oxo-4-phenyl-1,2-dihydro-isoquinolin-3-ylmethyl)-amide (42)

A solution of 41 (50 mg, 0.170 mmol), 5-phenylvaleric acid (33 mg, 0.187 mmol), 1-[3-(dimethylamino)propyl]-3-ethylcarbodiimide hydrochloride (36 mg, 0.187 mmol), 1-hydroxy-7-azabenzotriazole (25 mg, 0.187 mmol) in N,N-dimethylformamide was stirred at room temperature for 18 h. The contents of the reaction flask were poured into water and sat. sodium bicarbonate. Extracted with methylene chloride (3×). The combined organic extracts were washed with 5% potassium bisulfate, dried with sodium sulfate (anh.) and filtered. Concentration of the filtrate in vacuo followed by trituration with ether gave 42 as a white solid (62 mg, 140 mmol, 82.1%).

$^1$HNMR (CHCl$_3$, 300 MHz) δ 8.34 (d, 1H); 7.46–7.43 (m, 3H); 7.29–7.14 (m, 7H); 6.98–6.95 (m, 1H); 6.24 (d, 1H); 5.73 (s, 1H); 4.27 (d, 2H); 3.65 (s, 3H); 3.61 (s, 3H); 2.63 (m, 2H); 2.24 (m, 2H); 1.66 (m, 4H).

Compounds 43–97 were prepared using a procedure similar to that described for compound 42. These substances are summarized in Table 2.

EXAMPLE 20

Biphenyl-3-carboxylic acid (6-methoxy-2-methyl-1-oxo-4-phenyl-1,2-dihydro-isoquinolin-3-ylmethyl)-amide (96)

$^1$HNMR (CHCl$_3$, 300 MHz) δ 8.32 (d, 1H); 8.11 (s, 1H); 7.86–7.76 (m, 2H); 7.63 (m, 2H); 7.56–7.32 (m, 9H); 6.93 (m, 1H); 6.84 (s, br, 1H); 6.25 (d, 1H); 4.51 (d, 2H); 3.67 (s, 3H); 3.64 (s, 3H).

EXAMPLE 21

2-(5-Methoxy-2-methyl-1H-indol-3-yl)-N-(6-methoxy-2-methyl-1-oxo-4-phenyl-1,2-dihydro-isoquinolin-3-ylmethyl)-acetamide (97)

$^1$HNMR (CHCl$_3$, 300 MHz) δ 8.36 (d, 1H); 7.90 (s, 1H); 7.35–7.18 (m, 3H); 7.00 (m, 1H); 6.84 (m, 1H); 6.72 (m, 3H); 6.19 (m, 1H); 5.61 (m, 1H); 4.20 (d, 2H); 3.75 (s, 3H); 3.60 (m, 8H); 2.33 (s, 3H).

EXAMPLE 22

Reaction scheme of N-[2-(3-Dimethyaminomethyl-6-methoxy-1-oxo-4-phenyl-1H-isoquinolin--2-yl)-ethyl]-methanesulfonamide (117)

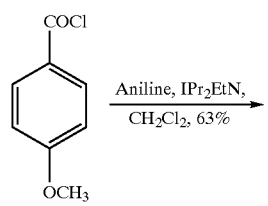

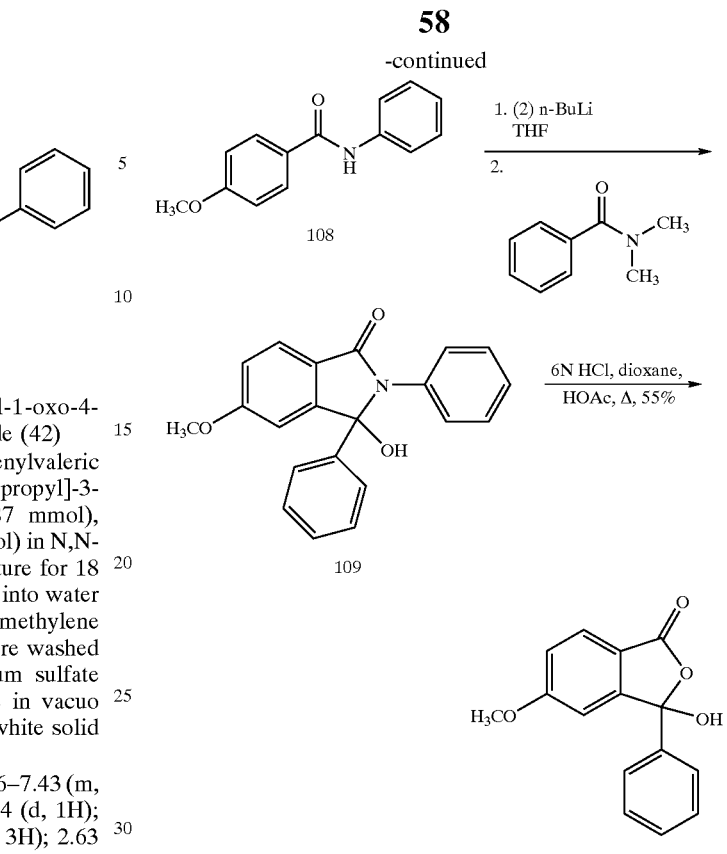

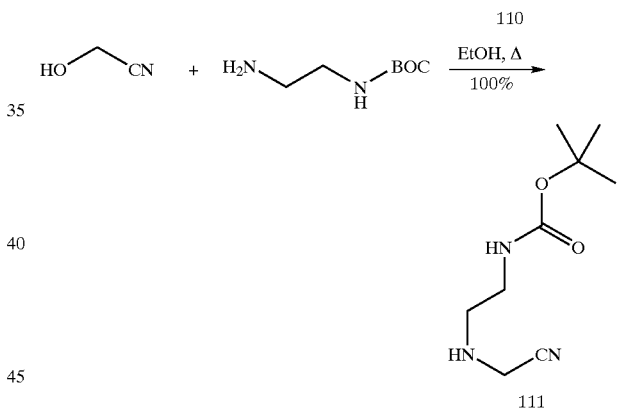

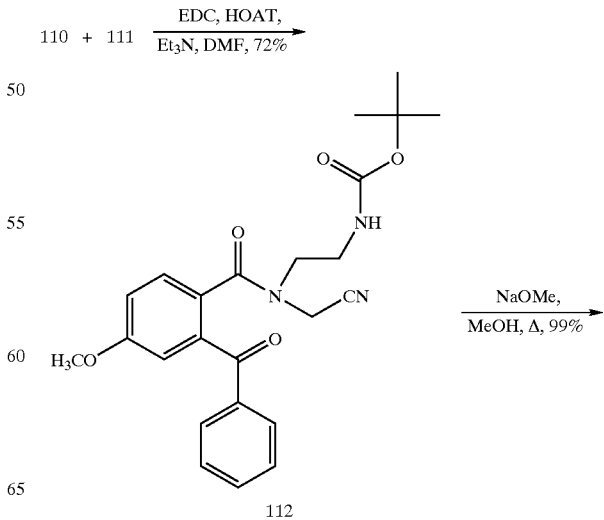

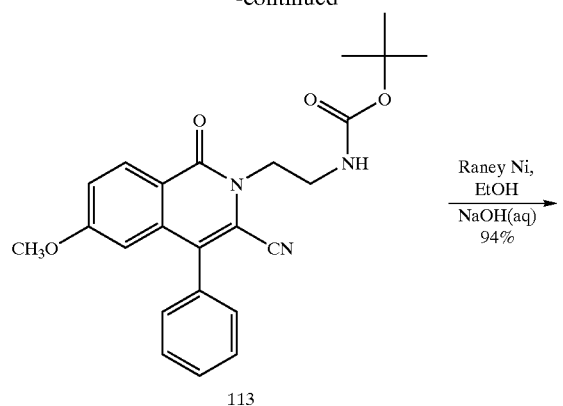

113

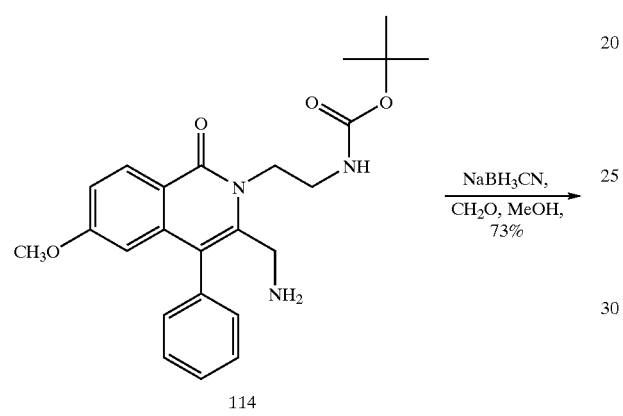

114

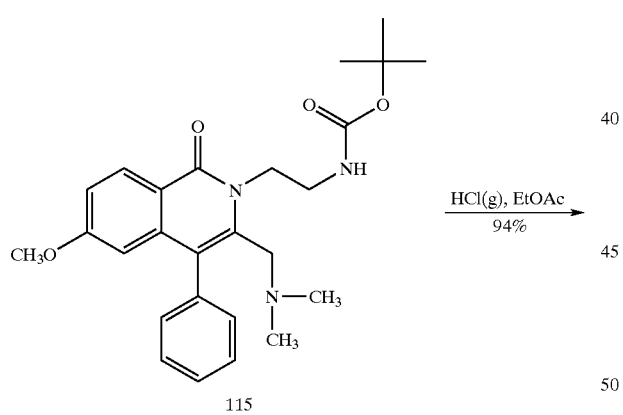

115

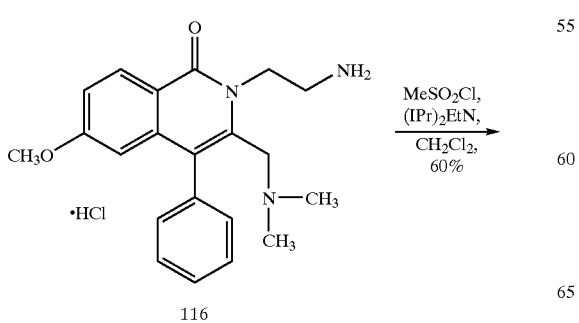

·HCl

116

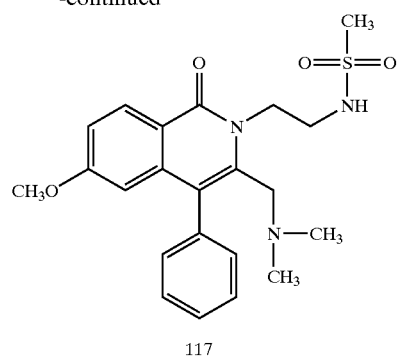

117

EXAMPLE 23

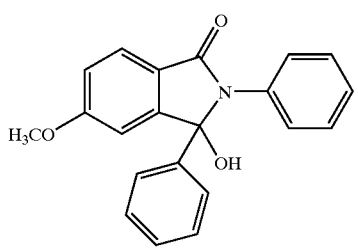

4-Methoxy-N-phenyl-benzamide (108)

p-Anisoyl chloride (10 g, 58.5 mmol) and methylene chloride (500 mL) were combined under Ar. Aniline (8.0 mL, 87.7 mmol) was added dropwise with stirring. Diisopropylethylamine (10.0 mL, 58.5 mmol) was added dropwise to give a white suspension. After 3 h the contents of the reaction flask were washed with 5% potassium bisulfate then sat. sodium bicarbonate. The organic portion was dried with sodium sulfate (anh.), filtered and evaporated in vacuo to give a solid. Trituration with ethyl acetate gave 108 as a white solid (3.37 g, 14.8 mmol, 25.4%).

$^1$HNMR (CHCl$_3$, 300 MHz) δ 7.88–7.82 (m, 2H); 7.74 (s, br, 1H); 7.66–7.60 (m, 2H); 7.42–7.34 (m, 2H), 7.18–7.10 (m, 1H); 7.02–6.94 (m, 2H); 3.88 (s, 3H).

EXAMPLE 24

3-Hydroxy-5-methoxy-2,3-diphenyl-2,3-dihydro-isoindol-1-one (109)

Combined under Ar 108 (3.00 g, 13.2 mmol) and tetrahydrofuran. Cooled in an IPA/dry ice bath. Added dropwise n-butyllithium solution (2.5M in hexanes, 11.1 mL, 27.8 mmol). Stirred 0.5 h with cooling then warmed over 0.5 h to −15° C. Recooled using IPA/dry ice and added a tetrahydrofuran solution of N,N-dimethylbenzamide (2.38 g, 15.8 mmol). Warmed to room temperature and quenched with water. Removed solvent in vacuo; added sat. sodium bicarbonate and extracted with ethyl acetate (3×). Dried combined organic portions with sodium sulfate (anh.), filtered, removed solvent in vacuo. A solid resulted which was triturated with ether to give 109 as a white solid (3.11 g, 9.39 mmol, 71.2%).

$^1$HNMR (CHCl$_3$, 300 MHz) δ 7.60 (d, 1H); 7.48–7.35 (m, 4H); 7.28–7.05 (m, 6H); 6.85 (m, 1H), 6.75 (m, 1H); 4.00 (s, 1H); 3.79 (s, 3H).

EXAMPLE 25

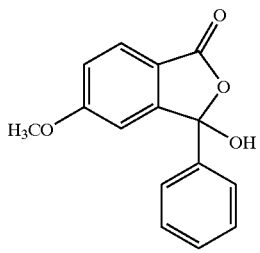

3-Hydroxy-5-methoxy-3-phenyl-3H-isobenzofuran-1-one (110)

A solution of 109 (3.11 g, 9.39 mmol), 6N hydrochloric acid (150 mL), and dioxane (150 mL) was heated at reflux under Ar for 18 h. Acetic acid (50 mL) was added and refluxing was continued for an additional 4 h. The organic solvents were removed in vacuo and the remaining aqueous was extracted with ethyl acetate (3×), washed with brine and dried with sodium sulfate (anh.). Filtration followed by removal of the solvent in vacuo gave 110 as a white solid (1.32 g, 5.16 mmol, 54.9%)

$^1$HNMR (CHCl$_3$, 300 MHz) δ 8.05 (d, 1H); 7.74 (d, 2H); 7.55 (m, 1H); 7.41 (m, 2H), 7.02 (m, 1H); 6.83 (m, 1H); 3.86 (s, 3H).

EXAMPLE 26

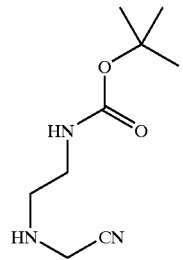

[2-(Cyanomethyl-amino)-ethyl]-carbamic acid tert-butyl ester (111)

Glycolonitrile (70%, 5.10 g, 62.5 mmol), tert-butyl-N-(2-aminoethyl)carbamate (10.0 g, 62.5 mmol), and ethanol (200 mL) were combined under Ar and heated at reflux for 4 h. Removal of the solvent in vacuo gave 111 as a yellow oil.

$^1$HNMR (CHCl$_3$, 300 MHz) δ 4.83 (s, br, 1H); 3.62 (s, 2H); 3.28 (m, 2H); 2.85 (m, 2H), 1.90 (s, br, 1H); 1.45 (s, 9H).

EXAMPLE 27

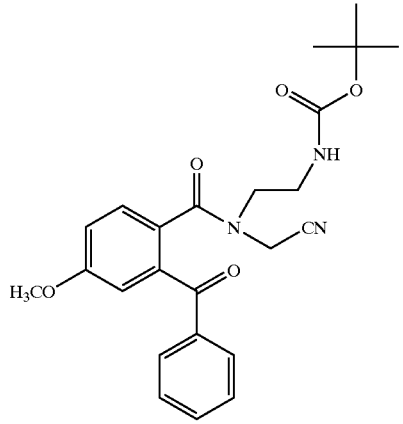

[2-(Cyanomethyl-{1-[4-methoxy-2-(1-phenyl-methanoyl)-phenyl]-methanoyl}-amino)-ethyl]-carbamic acid tert-butyl ester (112)

A solution of 110 (2.55 g, 9.96 mmol), 111 (2.38 g, 12.0 mmol), 1-[3-(dimethylamino)propyl]-3-ethylcarbodiimide hydrochloride (2.30 g, 12.0 mmol), 1-hydroxy-7-azabenzotriazole (1.63 g, 12.0 mmol) in N,N-dimethylformamide was stirred at room temperature for 4 days. The contents of the reaction flask were poured into water and sat. sodium bicarbonate. Extracted with methylene chloride (3×). The combined organic extracts were dried with sodium sulfate (anh.) and filtered. Concentration of the filtrate in vacuo followed flash column chromatography (hexane:ethyl acetate 60:40) gave 112 as a white foam (3.16 g, 7.23 mmol, 72.6%).

$^1$HNMR (CHCl$_3$, 300 MHz) δ 7.85 (d, 2H); 7.61 (m, 1H); 7.52–7.35 (m, 3H); 7.15–7.05 (m, 2H), 5.50 (s, br, 1H); 4.35 (m, 2H); 3.85 (s, 3H); 3.65 (m, 2H); 3.35 (m, 2H); 1.40 (s, 9H).

EXAMPLE 28

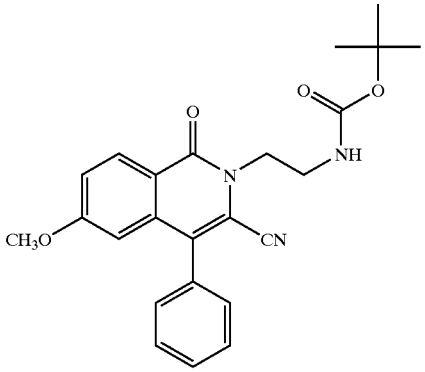

[2-(3-Cyano-6-methoxy-1-oxo-4-phenyl-1H-isoquinolin-2-yl)-ethyl]-carbamic acid tert-butyl ester (113)

A solution of 112 (3.16 g, 7.23 mmol), sodium methoxide (0.5M, 31.8 mL, 15.9 mmol) and methanol (100 mL) was heated at reflux for 1 h. The solvent was removed in vacuo and sat. sodium bicarbonate was added. Extracted with methylene chloride (3×). The combined organic extracts were dried with magnesium sulfate (anh.) and filtered. The filtrate was removed in vacuo to give 113 as a white solid (3.04 g, 7.23 mmol, 100%).

$^1$HNMR (CHCl$_3$, 300 MHz) δ 8.46 (d, 1H); 7.60–7.50 (m, 3H); 7.50–7.40 (m, 2H); 7.22 (dd, 1H), 6.66 (d, 1H); 5.00 (s, br, 1H); 4.45 (m, 2H); 3.75 (s, 3H); 3.65 (m, 2H); 1.30 (s, 9H).

EXAMPLE 29

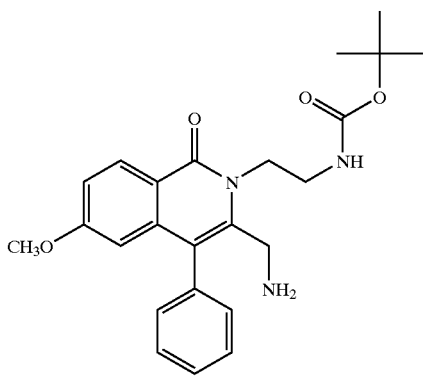

[2-(3-Aminomethyl-6-methoxy-1-oxo-4-phenyl-1H-isoquinolin-2-yl)-ethyl]-carbamic acid tert-butyl ester (114)

A suspension of 113 (3.04 g, 7.26 mmol), raney nickel, ammonium hydroxide (10 mL), and ethanol (50 mL) were combined in a Parr jar and hydrogenated at 55 psi for 18 h. The contents of the Parr jar were filtered through Celite and the filtrate was rotary evaporated to give 114 as a white solid (2.72 g, 6.43 mmol, 88.6%).

$^1$HNMR (CHCl$_3$, 300 MHz) δ 8.40 (d, 1H); 7.50 (m, 3H); 7.29 (m, 2H); 7.05 (m, 1H), 6.31 (s, 1H); 5.45 (s, br, 1H); 4.50 (m, 2H); 3.85–3.50 (m, 7H); 1.28 (s, 9H).

EXAMPLE 30

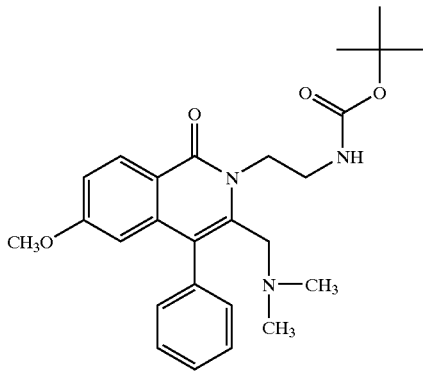

[2-(3-Dimethylaminomethyl-6-methoxy-1-oxo-4-phenyl-1H-isoquinolin-2-yl)-ethyl]-carbamic acid tert-butyl ester (115)

A solution of 114 (2.72 g, 6.43 mmol), formaldehyde (12.3M, 2.62 mL, 32.2 mmol), sodium cyanoborohydride (1.0M in tetrahydrofuran, 32.2 mL, 32.2 mmol), and methanol (100 mL) were heated at reflux for 1 h. The contents of the reaction flask were cooled and the solvent was removed in vacuo. Sat. sodium bicarbonate was added and the resulting mixture was extracted with ethyl acetate (3×). The combined organic extracts were dried with magnesium sulfate (anh.) and filtered. The filtrate was removed by rotary evaporation to give a colorless oil. Trituration with hexane:ether (1:1) gave 115 as a white solid (2.21 g, 4.90 mmol, 76.2%).

$^1$HNMR (CHCl$_3$, 300 MHz) δ 8.40 (d, 1H); 7.48 (m, 3H); 7.22 (m, 2H); 7.05 (dd, 1H), 6.30 (d, 1H); 5.70 (m, 1H); 4.55 (m, 2H); 3.66 (s, 3H); 3.52 (m, 2H); 3.35 (m, 2H); 2.13 (s, 6H); 1.40 (s, 9H).

EXAMPLE 31

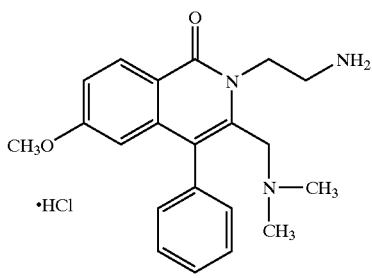

2-(2-Amino-ethyl)-3-dimethylaminomethyl-6-methoxy-4-phenyl-2H-isoquinolin-1-one (116)

A solution of 115 (1.71 g, 3.79 mmol) in ethyl acetate (200 mL) was cooled in an ice bath with stirring. Hydrogen chloride gas was bubbled through the solution for 15 min. then the contents of the reaction flask were warmed to room temperature. After 1.25 h the solvent was removed in vacuo and the remaining residue was triturated with ether to give 116 as a white solid (1.37 g, 3.54 mmol, 93.6%).

$^1$HNMR (CH$_3$OH, 300 MHz) δ 8.40 (d, 1H); 7.68–7.58 (m, 3H); 7.50–7.42 (m, 2H); 7.28 (dd, 1H), 4.60–4.46 (m, 4H); 3.50 (s, 3H); 3.36 (m, 2H); 2.80 (s, 6H).

EXAMPLE 32

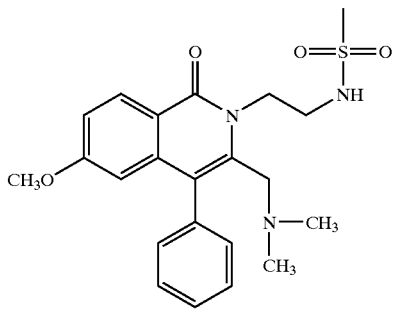

N-[2-(3-Dimethylaminomethyl-6-methoxy-1-oxo-4-phenyl-1H-isoquinolin-2-yl)-ethyl]-methanesulfonamide (117)

A solution of 116 (50 mg, 0.118 mmol), triethylamine (66 μL, 0.472 mmol), methanesulfonyl chloride (12 μL, 0.153 mmol) and methylene chloride (250 μL) were combined under Ar and stirred at room temperature 24 h. Added methylene chloride and washed the contents of the reaction flask with sat. sodium bicarbonate. Dried the organic layer with sodium sulfate (anh.), filtered then rotary evaporated the filtrate. Trituration of the resulting solid with ether gave 117 as a white solid (35 mg, 0.082 mmol, 69.1%).

$^1$HNMR (CHCl$_3$, 300 MHz) δ 8.40 (m, 2H); 7.54–7.44 (m, 3H); 7.20 (m, 2H); 7.06 (dd, 1H), 4.36 (m, 2H); 3.67 (m, 5H); 3.39 (s, 2H); 2.79 (s, 3H); 2.17 (s, 6H).

Compounds 118–132 were prepared using a procedure similar to that described for compound 117. These substances are summarized in Table 3.

EXAMPLE 33

Butane-1-sulfonic acid [2-(3-dimethylaminomethyl-6-methoxy-1-oxo-4-phenyl-1H-isoquinolin-2-yl)-ethyl]-amide (119)

$^1$HNMR (CHCl$_3$, 300 MHz) δ 8.40 (d, 1H); 8.23 (s, 1H); 7.48 (m, 3H); 7.20 (m, 2H); 7.05 (m, 1H); 6.30 (d, 1H); 4.37 (m, 2H); 3.68 (m, 5H); 3.40 (s, 2H); 2.88 (t, 2H); 2.18 (s, 6H); 1.59 (m, 2H); 1.25 (m, 2H); 0.73 (t, 3H).

EXAMPLE 34

Thiophene-2-sulfonic acid [2-(3-dimethylaminomethyl-6-methoxy-1-oxo-4-phenyl-1H-isoquinolin-2-yl)-ethyl]-amide (122)

$^1$HNMR (CHCl$_3$, 300 MHz) δ 9.50 (s, 1H); 8.37 (d, 1H); 7.50 (m, 4H); 7.20 (m, 2H); 7.12–7.03 (m, 2H); 6.77 (m, 1H); 6.25 (d, 1H); 4.34 (m, 2H); 3.69 (s, 3H); 3.60 (m, 2H); 3.37 (s, 2H); 2.23 (s, 6H).

EXAMPLE 35

N-[2-(3-Dimethylaminomethyl-6-methoxy-1-oxo-4-phenyl-1H-isoquinolin-2-yl)-ethyl]-4-methoxy-benzenesulfonamide (124)

$^1$HNMR (CHCl$_3$, 300 MHz) δ 8.51 (s, 1H); 8.26 (d, 1H); 7.62 (m, 2H); 7.48 (m, 4H); 7.15 m, 2H); 7.04 (m, 1H); 6.64 (m, 2H); 6.24 (d, 1H); 4.27 (m, 2H); 3.68 (s, 3H); 3.67 (s, 3H); 3.53 (m, 1H); 3.32 (s, 1H); 2.18 (s, 6H).

EXAMPLE 36

N-[2-(3-Dimethylaminomethyl-6-methoxy-1-oxo-4-phenyl-1H-isoquinolin-2-yl)-ethyl]-4-methyl-benzenesulfonamide (125)

$^1$HNMR (CHCl$_3$, 300 MHz) δ 8.60 (m, 1H); 8.26 (d, 1H); 7.58 (m, 2H); 7.46 (m, 3H); 7.15 (m, 2H); 7.04 (m, 1H); 6.96 (d, 2H); 6.24 (d, 1H); 4.45 (m, 2H); 3.69 (s, 3H); 3.54 (m, 2H); 3.62 (d, 2H); 2.19 (s, 9H).

EXAMPLE 37

1-Methyl-1H-imidazole-4-sulfonic acid [2-(3-dimethylaminomethyl-6-methoxy-1-oxo-4-phenyl-1H-isoquinolin-2-yl)-ethyl]-amide (127)

$^1$HNMR (CHCl$_3$, 300 MHz) δ 9.37 (s, 1H); 8.24 (d, 1H); 7.48 (m, 3H); 7.29 (m, 3H); 7.02 (m, 1H); 6.54 (s, 1H); 6.28 (m, 1H); 4.20 (m, 2H); 3.69 (s, 3H); 3.57 (m, 2H); 3.45 (s, 3H); 3.37 (s, 2H); 2.32 (s, 6H).

EXAMPLE 38

3,5-Dimethyl-isoxazole-4-sulfonic acid [2-(3-dimethylaminomethyl-6-methoxy-1-oxo-4-phenyl-1H-isoquinolin-2-yl)-ethyl]-amide (129)

$^1$HNMR (CHCl$_3$, 300 MHz) δ 9.31 (m, 1H); 8.35 (d, 1H); 7.49 (m, 3H); 7.20 (m, 2H); 7.08 (m, 1H); 6.30 (d, 1H); 4.31 (m, 2H); 3.69 (s, 3H); 3.49 (m, 2H); 3.40 (s, 2H); 2.59 (s, 3H); 2.27 (s, 3H); 2.40 (s, 6H).

What is claimed is:

1. A compound of structural Formula Ia:

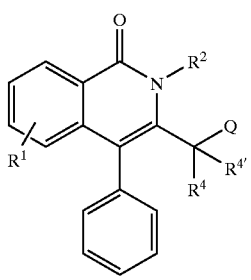

or a pharmaceutically acceptable salts, hydrates, solvates, crystal forms, or stereoisomers thereof, wherein:

R$^1$ is:
 (1) (C$_1$–C$_6$)-alkoxy,
 (2) (C$_1$–C$_4$)-perfluoroalkyl,
 (3) (C$_1$–C$_4$)-perfluoroalkoxy, or
 (4) halo, wherein halo is fluoro, chloro, bromo, or iodo;

R$^2$ is:
 (1) (C$_1$–C$_6$)-alkyl,
 (2) (CH$_2$)$_n$—(T)[S(O)$_m$]$_p$R$^3$, or
 (3) (CH$_2$)$_n$—(T)COR$^3$;

wherein T is —NH or

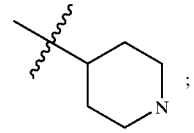

n is: 1, 2, or 3;
m is: 0, 1, or 2;
p is: 0 or 1;
R$^3$ is;
 (1) aryl, wherein aryl is defined as phenyl or naphthyl which is optionally substituted with one, two or three of the substituents selected from the group consisting of:
  (a) halo, wherein halo is fluoro, chloro, bromo, or iodo,
  (b) (C$_1$–C$_6$)-alkyl,
  (c) (C$_1$–C$_6$)-alkoxy,
  (d) (C$_1$–C$_4$)-perfluoroalkyl,
  (e) (C$_1$–C$_4$)-perfluoroalkoxy,
  (f) phenyl, and
  (g) benzyl;
 (2) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of:
  (a) halo, as defined above,
  (b) (C$_1$–C$_6$)-alkyl,
  (c) (C$_1$–C$_4$)-perfluoroalkyl, and
  (d) (C$_1$–C$_6$)-alkoxy;
 (3) (C$_1$–C$_6$)-alkyl optionally substituted with phenyl; or
 (4) (C$_1$–C$_6$)-alkoxy;

R$^4$ and R$^{4'}$ are independently:
 (1) H,
 (2) (C$_1$–C$_4$-alkyl,
 (3) (C$_3$–C$_7$)-cycloalkyl,
 (4) halo,
 (5) (C$_1$–C$_4$)-perfluoroalkyl, or
 (6) R$^4$ and R$^{4'}$ are taken together form a (C$_3$–C$_7$)-cycloalkyl ring;

Q is:
 (1) NR$^5$R$^6$, wherein R$^5$ and R$^6$ are independently:
  (a) H,
  (b) (C$_1$–C$_4$)-perfluoroalkyl,
  (c) (C$_3$–C$_7$)-cycloalkyl,
  (d) (C$_2$–C$_6$)-alkyl-aryl, wherein aryl is defined as phenyl or naphthyl which is substituted with one, two or three of the substituents selected from the group consisting of halo, hydroxy, (C$_1$–C$_6$)-alkyl, (C$_1$–C$_4$)-perfluoroalkyl, (C$_1$–C$_6$)-alkoxy, phenyl, phenoxy, and nitro, (e) $(C_1-C_{10})$-alkyl, which is optionally substituted with one, two, or three of the substituents selected from the group consisting of:
- (a') halo, wherein halo is fluoro, chloro, bromo, or iodo,
- (b') hydroxy,
- (c') oxo,
- (d') $(C_1-C_6)$-alkoxy,
- (e') phenyl, and
- (f') $(C_3-C_7)$-cycloalkyl; or (f) optionally, $R^5$ or $R^6$ can be joined with the $R^2$ substituent in Formula Ia to form a 5 to 8 atom heterocyclic ring, and the other of $R^5$ or $R^6$ is as defined above;

(2) heterocyclyl, wherein heterocyclyl is defined as a monocyclic or bicyclic ring of 5 to 10 carbon atoms which can be aromatic or nonaromatic, wherein the heterocyclyl is attached to the methylene bearing the $R^4$ and $R^5$ substituents through a N from the heterocyclyl and may optionally contain 1 to 3 additional heteroatoms selected from N, O or S and is optionally substituted with one, two, or three substituents selected from the group consisting of:
- (a) H,
- (b) $(C_1-C_6)$-alkyl,
- (c) $(C_1-C_4)$-perfluoroalkyl,
- (d) $(C_1-C_4)$-alkyl-aryl,
- (e) $CO_2(C_1-C_6)$-alkyl,
- (f) $CO_2H$
- (g) oxo, and
- (h) hydroxy; or (3) $NH(C=O)R^7$, wherein $R^7$ is:
- (a) $(C_1-C_{13})$-alkyl or $(C_1-C_{12})$-alkenyl, which is optionally substituted with one, two, or three substituents selected from the group consisting of:
  - (a') halo, wherein halo is fluoro, chloro, bromo, or iodo,
  - (b') hydroxy,
  - (c') oxo,
  - (d') nitro,
  - (e') $(C_1-C_6)$-alkoxy,
  - (f') $NR^5R^6$,
  - (g') $NH(CO)O(C_1-C_6)$-alkyl, wherein $(C_1-C_6)$-alkyl is optionally substituted with phenyl,
  - (h') $CO(C_1-C_{10})$-alkyl,
  - (i') $OC(O)(C_1-C_6)$-alkyl,
  - (j') $CONR^5R^6$,
  - (k') O-aryl, wherein aryl as defined in (o') below,
  - (l') S-aryl, wherein aryl as defined in (o') below,
  - (m') $(C_3-C_7)$-cycloalkyl, which is optionally substituted with 1 to 3 substituents selected from the group consisting of $(C_1-C_6)$-alkoxy, $CO(C_1-C_6)$-alkyl, oxo and $(C_1-C_6)$-alkyl optionally substituted with $NO_2$,
  - (n') $(C_5-C_7)$-cycloalkyl fused with phenyl, wherein $(C_5-C_7)$-cycloalkyl fused with phenyl is optionally substituted with 1 to 3 substituents selected from the group consisting of $(C_1-C_6)$-alkoxy, oxo, and $(C_1-C_6)$-alkyl,
  - (o') aryl, wherein aryl is defined as phenyl or naphthyl, which is optionally substituted with one, two or three of the substituents selected from the group consisting of:
    - (a") halo, as defined above,
    - (b") hydroxy,
    - (c") $(C_1-C_6)$-alkyl,
    - (d") $(C_1-C_4)$-perfluoroalkyl,
    - (e") $(C_1-C_6)$-alkoxy, optionally substituted with phenyl,
    - (f") phenyl,
    - (g") phenoxy, and
    - (h") nitro;
  - (p') heterocyclyl, wherein heterocyclyl is defined as a monocyclic, bicyclic, or tricyclic ring of 5 to 14 carbon atoms which can be aromatic or nonaromatic and containing from 1 to 3 heteroatoms selected from O, N or S, and the heterocyclyl being optionally substituted or with one, two, or three substituents selected from the group consisting of:
    - (a") H,
    - (b") halo, as defined above,
    - (c") $(C_1-C_6)$-alkyl,
    - (d") $(C_1-C_4)$-perfluoroalkyl,
    - (e") $(C_1-C_4)$-alkyl-aryl,
    - (f") $(C_1-C_6)$-alkoxy,
    - (g") phenyl,
    - (h") phenoxy,
    - (i") nitro,
    - (j") $CO_2(C_1-C_6)$-alkyl, and
    - (k") oxo; and
  - (q') S-heterocyclyl, wherein heterocyclyl as defined under (p') above;
- (b) aryl, wherein aryl is defined as phenyl or naphthyl which is optionally substituted with one, two or three of the substituents selected from the group consisting of:
  - (a') halo, wherein halo is fluoro, chloro, bromo, or iodo,
  - (b') $(C_1-C_6)$-alkyl,
  - (c') $(C_1-C_6)$-alkoxy,
  - (d') $(C_1-C_4)$-perfluoroalkyl;
  - (e') phenoxy,
  - (f') benzyl, and
  - (g') phenyl optionally substituted with $(C_1-C_4)$-perfluoroalkyl;
- (c) $(C_3-C_7)$-cycloalkyl, optionally substituted with phenyl; or
- (d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of:
  - (a') halo, as defined above,
  - (b') $(C_1-C_6)$-alkyl,
  - (c') $(C_1-C_4)$-perfluoroalkyl, and
  - (d') $(C_1-C_6)$-alkoxy.

2. The compound of Formula Ib,

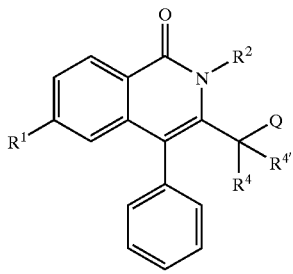

wherein the $R^1$, $R^2$, $R^4$, $R^{4'}$, and Q are as defined in claim 1.

3. The compound of Formula Ic, as recited in claim 2

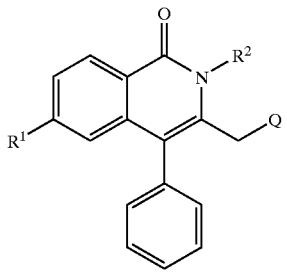

wherein $R^1$, $R^2$ and Q are as defined below:

$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;

$R^2$ is $(C_1-C_6)$-alkyl; and

Q is heterocyclyl which is selected from the group consisting of: pyrrolidinyl, piperazinyl, imidazolyl, morpholinyl, 1,4-dioxa-8-aza-spiro[4,5]decyl, piperidinyl, and 2,3-dihydroindolyl and the heterocyclyl is optionally substituted with one, two, or three substituents selected from the group consisting of H, $(C_1-C_4)$-alkyl, $CF_3$, benzyl, and $CO_2Et$.

4. The compound of Formula Id, as recited in claim 2

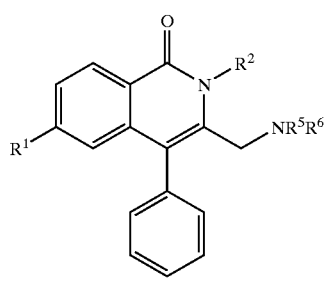

wherein $R^1$, $R^2$, $R^5$, and $R^6$ are as defined below:

$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;

$R^2$ is $(C_1-C_6)$-alkyl; and $R^5$ and $R^6$ are independently: $(C_1-C_{10})$-alkyl optionally substituted with $(C_3-C_7)$-cycloalkyl, $(C_1-C_4)$-perfluoroalkyl, and phenyl.

5. The compound of Formula Ie, as recited in claim 2

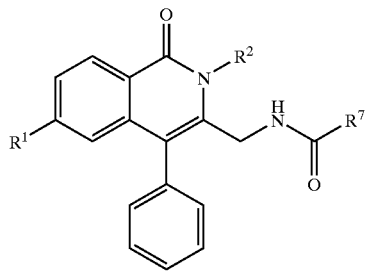

wherein $R^1$, $R^2$, and $R^7$ are as defined below:

$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;

$R^2$ is $(C_1-C_6)$-alkyl; and $R^7$ is:
(a) $(C_1-C_{13})$-alkyl or $(C_1-C_{12})$-alkenyl, which is optionally substituted with one, two, or three substituents selected from the group consisting of:
(a') hydroxy,
(b') oxo,
(c') $NR^5R^6$,
(d') $NH(CO)O(C_1-C_6)$-alkyl, wherein $(C_1-C_6)$-alkyl is optionally substituted with phenyl,
(e') $CO(C_1-C_{10})$-alkyl,
(f') $OC(O)(C_1-C_6)$-alkyl,
(g') $CONR^5R^6$,
(h') O-aryl, wherein aryl as defined in (l') below,
(i') S-aryl, wherein aryl as defined in (l') below,
(j') $(C_3-C_7)$-cycloalkyl, which is optionally substituted with 1 to 3 substituents selected from the group consisting of $(C_1-C_6)$-alkoxy, $CO(C_1-C_6)$-alkyl, and oxo, and $(C_1-C_6)$-alkyl optionally substituted with $NO_2$,
(k') $(C_5-C_7)$-cycloalkyl fused with phenyl, wherein $(C_5-C_7)$-cycloalkyl fused with phenyl is optionally substituted with 1 to 3 substituents selected from the group consisting of $(C_1-C_6)$-alkoxy, oxo, and $(C_1-C_6)$-alkyl,
(l') aryl, wherein aryl is defined as phenyl or naphthyl, which is optionally substituted with one, two or three of the substituents selected from the group consisting of:
(a") halo, as defined above,
(b") hydroxy,
(c") $(C_1-C_6)$-alkyl,
(d") $(C_1-C_4)$-perfluoroalkyl,
(e") $(C_1-C_6)$-alkoxy, optionally substituted with phenyl,
(f") phenyl,
(g") phenoxy, and
(h") nitro;
(m') heterocyclyl, wherein heterocyclyl is defined as a monocyclic, bicyclic, or tricyclic ring of 5 to 14 carbon atoms which can be aromatic or nonaromatic and containing from 1 to 3 heteroatoms selected from O, N or S, and the heterocyclyl being optionally substituted or with one, two, or three substituents selected from the group consisting of:
(a") H,
(b") halo, as defined above,
(c") $(C_1-C_6)$-alkyl,
(d") $(C_1-C_4)$-perfluoroalkyl, (e") $(C_1-C_4)$-alkyl-aryl,
(f") $(C_1-C_6)$-alkoxy,
(g") phenyl,
(h") phenoxy,
(i") nitro,
(j") $CO_2(C_1-C_6)$-alkyl, and
(k") oxo; and
(n') S-heterocyclyl, wherein heterocyclyl as defined under (m') above;
(b) aryl, wherein aryl is defined as phenyl or naphthyl which is optionally substituted with one, two or three of the substituents selected from the group consisting of:
(a') halo, wherein halo is fluoro, chloro, bromo, or iodo,
(b') $(C_1-C_6)$-alkoxy,
(c') phenoxy,
(d') benzyl, and
(e') phenyl optionally substituted with $(C_1-C_4)$-perfluoroalkyl;
(c) $(C_3-C_7)$-cycloalkyl, optionally substituted with phenyl; or
(d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of:
(a') halo, as defined above,
(b') $(C_1-C_6)$-alkyl,
(c') $(C_1-C_4)$-perfluoroalkyl, and
(d') $(C_1-C_6)$-alkoxy.

6. The compound of Formula If, as recited in claim 2

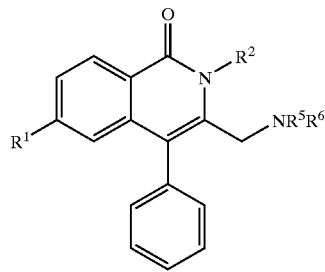

If wherein $R^1$, $R^2$, $R^3$, $R^5$, $R^6$, and n are as defined below:
$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;
$R^2$ is $(CH_2)_n(T)SO_2R^3$ or $(CH_2)_n(T)COR^3$,
$R^3$ is:
(a) $(C_1-C_6)$-alkyl optionally substituted with phenyl;
(b) phenyl or naphthyl optionally substituted with one, two, or three substituents selected from the group consisting of $OCF_3$, $O(CH_3)_3$, $CH_3$, $CF_3$ and halo;
(c) $(C_1-C_6)$-alkoxy; and
(d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents selected from the group consisting of $(C_1-C_6)$-alkyl and $(C_1-C_6)$-alkoxy;
$R^5$ and $R^6$ are independently:
(a) $(C_1-C_4)$-perfluoroalkyl,
(b) phenyl, and
(c) $(C_1-C_{10})$-alkyl optionally substituted with $(C_3-C_7)$-cycloalkyl; and
n is 1, 2, or 3.

7. The compound of Formula Ig, as recited in claim 2

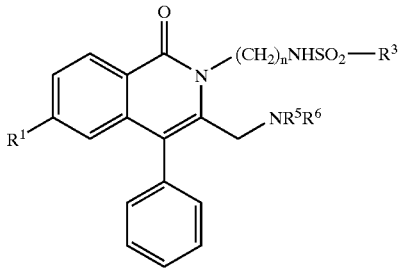

Ig wherein $R^1$, $R^3$, $R^5$, $R^6$, and n are as defined below:
$R^1$ is $(C_1-C_6)$-alkoxy, $(C_1-C_4)$-perfluoroalkyl, $(C_1-C_4)$-perfluoroalkoxy, or halo, wherein halo is fluoro, chloro, bromo, or iodo;
$R^3$ is:
(a) $(C_1-C_6)$-alkyl optionally substituted with phenyl;
(b) phenyl or naphthyl optionally substituted with one, two, or three substituents selected from the group consisting of $OCF_3$, $O(CH_3)_3$, $CH_3$, $CF_3$ and halo;
(c) $(C_1-C_6)$-alkoxy; and
(d) heteroaryl, wherein heteroaryl is defined as a monocyclic or bicyclic aromatic ring of 5 to 10 carbon atoms containing from 1 to 3 heteroatoms selected from O, N or S, and heteroaryl being optionally substituted with one, two, or three substituents of $(C_1-C_6)$-alkyl;
$R^5$ and $R^6$ are independently:
(a) $(C_1-C_4)$-perfluoroalkyl,
(b) phenyl, and
(c) $(C_1-C_{10})$-alkyl optionally substituted with $(C_3-C_7)$-cycloalkyl; and
n is 1, 2, or 3.

8. The compound of claim 2 wherein the compound is selected from the group consisting of:
3-dimethylaminomethyl-6-methoxy-2-methyl-4-phenyl-2H-isoquinoline-1-one;
3-(2,3-dihydro-indol-1-ylmethyl)-6-methoxy-2-methyl-4-phenyl-2H-isoquinoline-1-one;
3-[(ethyl-methyl-amino)-methyl]-6-methoxy-2-methyl-4-phenyl-2H-isoquinoline-1-one;
6-methoxy-2-methyl-4-phenyl-3-piperidin-1-ylmethyl-2H-isoquinoline-1-one;
3-[(tert-butyl-methyl-amino)-methyl]-6-methoxy-2-methyl-4-phenyl-2H-isoquinoline-1-one;
3-[(isopropyl-methyl-amino)-methyl]-6-methoxy-2-methyl-4-phenyl-2H-isoquinoline-1-one;
3-[(isopropyl-methyl-amino)-methyl]-6-methoxy-2-methyl-4-phenyl-2H-isoquinoline-1-one;
6-methoxy-2-methyl-4-phenyl-3-[(2,2,2-trifluoro-ethylamino)-methyl]-2H-isoquinoline-1-one;
2-(5-methoxy-2-methyl-1H-indol-3-yl)-N-(6-methoxy-2-methyl-1-oxo-4-phenyl-1,2-dihydro-isoquinoline-3-ylmethyl)-acetamide;
N-[2-(3-dimethylaminomethyl-6-methoxy-1-oxo-4-phenyl-1H-isoquinoline-2-yl)-ethyl]-methanesulfonamide;
butane-1-sulfonic acid [2-(3-dimethylaminomethyl-6-methoxy-1-oxo-4-phenyl-1H-isoquinolin-2-yl)-ethyl]-amide;
thiophene-2-sulfonic acid [2-(3-dimethylaminomethyl-6-methoxy-1-oxo-4-phenyl-1H-isoquinolin-2-yl)-ethyl]-amide;
N-[2-(3-dimethylaminomethyl-6-methoxy-1-oxo-4-phenyl-1H-isoquinolin-2-yl)-ethyl]-benzenesulfonamide;

furan-2-carboxylic acid [2-(3-dimethylaminomethyl-6-methoxy-1-oxo-4-phenyl-1H-isoquinolin-2-yl)-ethyl]-amide;

N-[2-(3-dimethylaminomethyl-6-methoxy-1-oxo-4-phenyl-1H-isoquinolin-2-yl)-ethyl]-2-phenyl-acetamide hydrochloride;

N-[2-(3-dimethylaminomethyl-6-methoxy-1-oxo-4-phenyl-1H-isoquinolin-2-yl)-ethyl]-nicotinamide;

9-methoxy-2-methyl-11-phenyl-1,2,3,4-tetrahydro-pyrazino[1,2-b]isoquinolin-6-one;

2-(1-acetyl-peperidin-4-ylmethyl)-3-dimethylaminomethyl-6-methoxy-4-phenyl-2H-isoquinolin-1-one;

3-dimethylaminomethyl-2-(1-methanesulfonyl-piperidin-4-ylmethyl)-6-methoxy-4-phenyl-2H-isoquinolin-1-one;

[2-(3-dimethylaminomethyl-6-methoxy-1-oxo-4-phenyl-1H-isoquinolin-2-yl)-ethyl]-carbamic acid tert-butyl ester;

N-[2-(3-dimethylaminomethyl-6-methoxy-1-oxo-4-phenyl-1H-isoquinolin-2-yl)-ethyl]-isonicotinamide; and

[2-(3-aminomethyl-6-methoxy-1-oxo-4-phenyl-1H-isoquinolin-2-yl)-ethyl]-carbamic acid tert-butyl ester.

9. The compound of claim 2 wherein the compound is 3-dimethylaminomethyl-6-methoxy-2-methyl-4-phenyl-2H-isoquinolin-1-one or a pharmaceutically acceptable salt, hydrate, solvate, crystal forms and stereoisomer thereof as shown below:

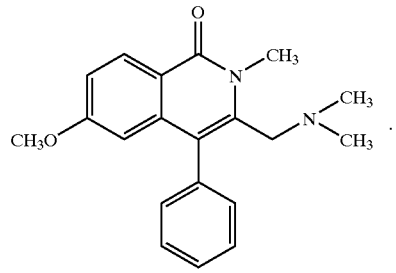

10. A pharmaceutical composition for the treatment of an atrial arrhythmia, comprising a pharmaceutically acceptable carrier and at least one compound of Formula I or its pharmaceutically acceptable salt, hydrate, solvate, crystal form, and stereoisomer thereof as recited in claim 1.

* * * * *